(12) United States Patent
Oddsson et al.

(10) Patent No.: US 8,801,802 B2
(45) Date of Patent: Aug. 12, 2014

(54) SYSTEM AND METHOD FOR DATA COMMUNICATION WITH A MECHATRONIC DEVICE

(75) Inventors: Magnús Oddsson, Hafnarfirdi (IS); Arinbjörn V. Clausen, Reykjavik (IS)

(73) Assignee: Össur hf, Reykjavik (IS)

(*) Notice: Subject to any disclaimer, the term of this patent is extended or adjusted under 35 U.S.C. 154(b) by 1005 days.

(21) Appl. No.: 11/355,058

(22) Filed: Feb. 15, 2006

(65) Prior Publication Data

US 2006/0184252 A1 Aug. 17, 2006

Related U.S. Application Data

(60) Provisional application No. 60/653,717, filed on Feb. 16, 2005, provisional application No. 60/679,953, filed on May 10, 2005.

(51) Int. Cl.
*A61F 2/68* (2006.01)
*A61F 2/60* (2006.01)

(52) U.S. Cl.
USPC .................................. 623/27; 623/24; 623/40

(58) Field of Classification Search
CPC ........ A61F 2/66; A61F 2/68; A61F 2002/704
USPC ................................................ 623/24, 27, 40
See application file for complete search history.

(56) References Cited

U.S. PATENT DOCUMENTS

| 2,568,051 A | 9/1951 | Catranis |
| 2,619,652 A | 12/1952 | Vesper |
| 2,843,853 A | 7/1958 | Mauch |
| 2,859,451 A | 11/1958 | Mauch |
| 3,316,558 A | 5/1967 | Mortensen |
| 3,417,409 A | 12/1968 | Prahl |

(Continued)

FOREIGN PATENT DOCUMENTS

| CH | 543277 | 12/1973 |
| CN | 2043873 | 9/1989 |

(Continued)

OTHER PUBLICATIONS

Int'l Search Report for International application No. PCT/US2006/005352, Dated Dec. 28, 2006.

(Continued)

*Primary Examiner* — Bruce E Snow
*Assistant Examiner* — Melissa Hoban
(74) *Attorney, Agent, or Firm* — Knobbe, Martens, Olson & Bear, LLP

(57) ABSTRACT

Embodiments include a system for controlling motion of a human limb. The system may include a plurality of mechatronic devices, each of which may be in communication with at least one other of the plurality of mechatronic devices. Each of the mechatronic devices includes one or more of a processor, an actuator, or a sensor. One or more of the mechatronic devices may be configured to generate a control state for at least one other of the plurality of mechatronic devices based on the communicated data. In one embodiment, the communicated data is used to synchronize the mechatronic devices. In one embodiment, one or more of the mechatronic devices is configured to receive executable instructions for controlling an actuator via a communications interface.

21 Claims, 12 Drawing Sheets

(56) References Cited

U.S. PATENT DOCUMENTS

| | | |
|---|---|---|
| 3,501,776 A | 3/1970 | Beeker et al. |
| 3,659,294 A | 5/1972 | Glabiszewski |
| 3,701,368 A | 10/1972 | Stern |
| 3,791,375 A | 2/1974 | Pfeifer |
| 3,820,168 A | 6/1974 | Horvath |
| 3,866,246 A | 2/1975 | Seamone et al. |
| 3,871,032 A | 3/1975 | Karas |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,386,891 A | 6/1983 | Riefel et al. |
| 4,387,472 A | 6/1983 | Wilson |
| 4,433,679 A | 2/1984 | Mauldin et al. |
| 4,458,367 A | 7/1984 | May |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | PetrofskR |
| 4,569,352 A | 2/1986 | Petrofsky et al. |
| 4,578,083 A | 3/1986 | Williams |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,711,450 A | 12/1987 | McArthur |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Roung et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,989,161 A | 1/1991 | Oaki |
| 4,994,086 A | 2/1991 | Edwards |
| 5,012,591 A | 5/1991 | Asakawa |
| 5,020,790 A | 6/1991 | Beard et al. |
| 5,033,291 A | 7/1991 | Podoloff et al. |
| 5,044,360 A | 9/1991 | Janke |
| 5,062,673 A | 11/1991 | Mimura |
| 5,062,856 A | 11/1991 | Sawamura et al. |
| 5,062,857 A | 11/1991 | Berringer et al. |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe et al. |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnäs |
| 5,323,650 A | 6/1994 | Fullen et al. |
| 5,327,790 A | 7/1994 | Levin et al. |
| 5,336,269 A | 8/1994 | Smits |
| 5,357,696 A | 10/1994 | Gray et al. |
| 5,376,128 A | 12/1994 | Bozeman, Jr. |
| 5,376,133 A | 12/1994 | Gramnäs |
| 5,376,137 A | 12/1994 | Shorter et al. |
| 5,382,373 A | 1/1995 | Carlson et al. |
| 5,383,939 A | 1/1995 | James |
| 5,394,132 A | 2/1995 | Poil |
| 5,397,287 A | 3/1995 | Lindfors |
| 5,398,917 A | 3/1995 | Carlson et al. |
| 5,405,407 A | 4/1995 | Kodama et al. |
| 5,405,409 A | 4/1995 | Knoth |
| 5,405,410 A | 4/1995 | Arbogast et al. |
| 5,408,873 A | 4/1995 | Schmidt et al. |
| 5,413,611 A | 5/1995 | Haslam, II et al. |
| 5,422,558 A | 6/1995 | Stewart |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,458,655 A | 10/1995 | Bozeman, Jr. |
| 5,472,412 A | 12/1995 | Knoth |
| 5,476,441 A | 12/1995 | Durfee et al. |
| 5,480,454 A | 1/1996 | Bozeman, Jr. |
| 5,504,415 A | 4/1996 | PodrazhanskR et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford et al. |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer et al. |

(56) References Cited

U.S. PATENT DOCUMENTS

| | | |
|---|---|---|
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,561 A | 9/1998 | Rodriguez |
| 5,800,568 A | 9/1998 | Atkinson et al. |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | Van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Conner |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allum |
| 5,929,332 A | 7/1999 | Brown |
| 5,941,913 A | 8/1999 | Woolnough et al. |
| 5,947,238 A | 9/1999 | Jolly et al. |
| 5,948,021 A | 9/1999 | Radcliffe |
| 5,955,667 A | 9/1999 | Fyfe |
| 5,957,981 A | 9/1999 | Gramnäs |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,998,930 A | 12/1999 | UpadhRaR et al. |
| 6,006,412 A | 12/1999 | Bergmann et al. |
| 6,007,582 A | 12/1999 | May |
| RE36,521 E | 1/2000 | Hiemisch |
| 6,027,664 A | 2/2000 | Weiss et al. |
| 6,039,091 A | 3/2000 | Rodgers et al. |
| 6,061,577 A | 5/2000 | Andrieu et al. |
| 6,080,123 A | 6/2000 | Pansiera |
| 6,086,616 A | 7/2000 | Okuda et al. |
| 6,091,977 A | 7/2000 | Tarjan et al. |
| 6,093,162 A | 7/2000 | Fairleigh et al. |
| 6,095,486 A | 8/2000 | Ivers et al. |
| 6,113,642 A | 9/2000 | Petrofsky et al. |
| 6,117,177 A | 9/2000 | Chen et al. |
| 6,129,690 A | 10/2000 | Hamlin et al. |
| 6,129,766 A | 10/2000 | Johnson et al. |
| 6,139,586 A | 10/2000 | Wagner et al. |
| 6,165,226 A | 12/2000 | Wagner |
| 6,168,634 B1 | 1/2001 | Schmitz |
| 6,183,425 B1 | 2/2001 | Whalen et al. |
| 6,187,051 B1 | 2/2001 | van de Veen |
| D439,339 S | 3/2001 | Sawatzki |
| 6,195,921 B1 | 3/2001 | Truong |
| 6,206,932 B1 | 3/2001 | Johnson |
| 6,206,933 B1 | 3/2001 | Shorter et al. |
| 6,206,934 B1 | 3/2001 | Phillips |
| 6,241,775 B1 | 6/2001 | Blatchford |
| D446,304 S | 8/2001 | Sawatzki |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundel |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,485,519 B2 | 11/2002 | Meyers et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,522,266 B1 | 2/2003 | Soehren et al. |
| 6,537,322 B1 | 3/2003 | Johnson et al. |
| 6,587,728 B2 | 7/2003 | Fang et al. |
| 6,589,287 B2 | 7/2003 | Lundborg |
| 6,599,439 B2 | 7/2003 | Iregar et al. |
| 6,602,295 B1 | 8/2003 | Doddroe et al. |
| 6,610,101 B2 | 8/2003 | Herr et al. |
| 6,613,097 B1 | 9/2003 | Cooper |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,695,885 B2 | 2/2004 | Schulman et al. |
| 6,719,806 B1 | 4/2004 | Zahedi et al. |
| 6,733,180 B2 | 5/2004 | Nakamura |
| 6,740,123 B2 | 5/2004 | Davalli et al. |
| 6,743,260 B2 | 6/2004 | Townsend et al. |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,770,045 B2 | 8/2004 | Naft et al. |
| 6,805,677 B2 | 10/2004 | Simmons |
| 6,811,571 B1 | 11/2004 | Phillips |
| 6,813,582 B2 | 11/2004 | Levi et al. |
| D499,487 S | 12/2004 | Bedard et al. |
| D501,925 S | 2/2005 | Bedard et al. |
| 6,855,170 B2 | 2/2005 | Gramnas |
| 6,875,241 B2 | 4/2005 | Christensen |
| 6,876,135 B2 | 4/2005 | Pelrine |
| 6,908,488 B2 | 6/2005 | Passivaara |
| 6,918,308 B2 | 7/2005 | Biedermann |
| 6,955,692 B2 | 10/2005 | Grundei |
| 6,966,933 B2 | 11/2005 | Christensen |
| 7,029,500 B2 | 4/2006 | Martin |
| 7,063,727 B2 | 6/2006 | Van Phillips et al. |
| 7,066,896 B1 | 6/2006 | Kiselik |
| 7,101,487 B2 | 9/2006 | Hsu et al. |
| 7,118,601 B2 | 10/2006 | Yasui et al. |
| 7,131,998 B2 | 11/2006 | Pasolini |
| 7,137,998 B2 | 11/2006 | Bedard et al. |
| 7,147,667 B2 | 12/2006 | Bedard |
| 7,150,762 B2 | 12/2006 | Caspers |
| 7,164,967 B2 | 1/2007 | Etienne-Cummings et al. |
| 7,198,071 B2 | 4/2007 | Bisbee, III et al. |
| 7,295,892 B2 | 11/2007 | Herr et al. |
| 7,314,490 B2 | 1/2008 | Bedard et al. |
| 7,381,192 B2 | 6/2008 | Brodard |
| 7,396,337 B2 | 7/2008 | McBean et al. |
| 7,410,338 B2 | 8/2008 | Schiele et al. |
| 7,410,471 B1 | 8/2008 | Campbell et al. |
| 7,410,472 B2 | 8/2008 | Yakimovich et al. |
| 7,431,737 B2 | 10/2008 | Ragnarsdottir et al. |
| 7,455,696 B2 | 11/2008 | Bisbee, III et al. |
| 7,531,006 B2 | 5/2009 | Clausen et al. |
| 7,575,602 B2 | 8/2009 | Amirouche et al. |
| 7,637,957 B2 | 12/2009 | Ragnarsdottir et al. |
| 7,637,959 B2 | 12/2009 | Clausen et al. |
| 7,691,154 B2 | 4/2010 | Asgeirsson et al. |
| 7,794,505 B2 | 9/2010 | Clausen et al. |
| 7,811,333 B2 | 10/2010 | Jónsson et al. |
| 7,815,689 B2 | 10/2010 | Bedard et al. |
| 7,862,620 B2 | 1/2011 | Clausen et al. |
| 7,867,285 B2 | 1/2011 | Clausen et al. |
| 7,896,927 B2 | 3/2011 | Clausen et al. |
| 7,918,808 B2 | 4/2011 | Simmons |
| 7,955,398 B2 | 6/2011 | Bedard et al. |
| 8,007,544 B2 | 8/2011 | Jonsson et al. |
| 8,048,007 B2 | 11/2011 | Roy |
| 8,057,550 B2 | 11/2011 | Clausen |
| 8,075,633 B2 | 12/2011 | Herr et al. |
| 8,122,772 B2 | 2/2012 | Clausen et al. |
| 8,142,370 B2 | 3/2012 | Weinberg et al. |
| 8,287,477 B1 | 10/2012 | Herr et al. |
| 8,323,354 B2 | 12/2012 | Bedard et al. |
| 2001/0029400 A1 | 10/2001 | Deffenbaugh et al. |

(56) References Cited

U.S. PATENT DOCUMENTS

| | | |
|---|---|---|
| 2002/0040601 A1 | 4/2002 | Fyfe et al. |
| 2002/0052663 A1 | 5/2002 | Herr et al. |
| 2002/0087216 A1 | 7/2002 | Atkinson et al. |
| 2002/0103543 A1 | 8/2002 | Asai et al. |
| 2002/0138153 A1 | 9/2002 | Koniuk |
| 2002/0183803 A1 | 12/2002 | Fang et al. |
| 2002/0198604 A1 | 12/2002 | Schulman et al. |
| 2003/0019700 A1 | 1/2003 | Wittig |
| 2003/0029247 A1 | 2/2003 | Biedermann |
| 2003/0067245 A1 | 4/2003 | Pelrine et al. |
| 2003/0093158 A1 | 5/2003 | Phillips et al. |
| 2003/0120353 A1 | 6/2003 | Christensen |
| 2003/0163206 A1* | 8/2003 | Yasui et al. ............... 623/24 |
| 2004/0039454 A1 | 2/2004 | Herr et al. |
| 2004/0044417 A1 | 3/2004 | Gramnas |
| 2004/0049290 A1 | 3/2004 | Bedard |
| 2004/0054423 A1 | 3/2004 | Martin |
| 2004/0064195 A1 | 4/2004 | Herr |
| 2004/0083007 A1 | 4/2004 | Molino et al. |
| 2004/0088057 A1 | 5/2004 | Bedard |
| 2004/0102723 A1 | 5/2004 | Horst |
| 2004/0111163 A1 | 6/2004 | Bedard et al. |
| 2004/0181289 A1 | 9/2004 | Bedard et al. |
| 2004/0193286 A1 | 9/2004 | Grundei |
| 2004/0215111 A1* | 10/2004 | Bonutti et al. ............... 601/5 |
| 2004/0217324 A1 | 11/2004 | Hsu et al. |
| 2004/0263127 A1 | 12/2004 | Turner et al. |
| 2004/0267379 A1 | 12/2004 | Pasolini |
| 2005/0004495 A1 | 1/2005 | Goswami |
| 2005/0010139 A1 | 1/2005 | Aminian et al. |
| 2005/0038524 A1 | 2/2005 | Jonsson et al. |
| 2005/0107889 A1 | 5/2005 | Bedard et al. |
| 2005/0119763 A1 | 6/2005 | Christensen |
| 2005/0137717 A1 | 6/2005 | Gramnas et al. |
| 2005/0143838 A1 | 6/2005 | Collier |
| 2005/0192677 A1 | 9/2005 | Ragnarsdottir et al. |
| 2005/0197717 A1 | 9/2005 | Ragnarsdottir et al. |
| 2005/0216097 A1 | 9/2005 | Rifkin |
| 2005/0234562 A1 | 10/2005 | Okuda et al. |
| 2005/0283257 A1 | 12/2005 | Bisbee, III et al. |
| 2006/0041321 A1 | 2/2006 | Christensen |
| 2006/0064195 A1 | 3/2006 | Kern et al. |
| 2006/0069448 A1 | 3/2006 | Yasui |
| 2006/0122710 A1 | 6/2006 | Bedard |
| 2006/0122711 A1 | 6/2006 | Bedard et al. |
| 2006/0136072 A1 | 6/2006 | Bisbee et al. |
| 2006/0155385 A1 | 7/2006 | Martin |
| 2006/0184252 A1 | 8/2006 | Oddsson et al. |
| 2006/0184280 A1 | 8/2006 | Oddsson et al. |
| 2006/0195197 A1 | 8/2006 | Clausen et al. |
| 2006/0201757 A1 | 9/2006 | Dupuis et al. |
| 2006/0224246 A1 | 10/2006 | Clausen et al. |
| 2006/0224247 A1 | 10/2006 | Clausen et al. |
| 2006/0235544 A1 | 10/2006 | Iversen et al. |
| 2006/0249315 A1 | 11/2006 | Herr et al. |
| 2007/0016329 A1 | 1/2007 | Herr et al. |
| 2007/0027555 A1 | 2/2007 | Palmer et al. |
| 2007/0027557 A1 | 2/2007 | Jonsson et al. |
| 2007/0043449 A1 | 2/2007 | Herr et al. |
| 2007/0050045 A1 | 3/2007 | Clausen et al. |
| 2007/0050047 A1 | 3/2007 | Ragnarsdottir et al. |
| 2007/0123997 A1 | 5/2007 | Herr et al. |
| 2007/0156252 A1 | 7/2007 | Jonsson et al. |
| 2007/0162152 A1 | 7/2007 | Herr et al. |
| 2008/0046096 A1 | 2/2008 | Bedard et al. |
| 2008/0058959 A1 | 3/2008 | Bedard et al. |
| 2008/0215161 A1 | 9/2008 | Ragnarsdottir et al. |
| 2009/0143870 A1 | 6/2009 | Bedard et al. |
| 2009/0299480 A1 | 12/2009 | Gilbert et al. |
| 2010/0185124 A1 | 7/2010 | Bisbee, III et al. |
| 2010/0262260 A1 | 10/2010 | Bedard et al. |
| 2010/0324456 A1 | 12/2010 | Jonsson et al. |
| 2010/0324699 A1 | 12/2010 | Herr et al. |
| 2011/0106274 A1 | 5/2011 | Ragnarsdottir et al. |
| 2011/0130847 A1 | 6/2011 | Bedard et al. |
| 2011/0137429 A1 | 6/2011 | Bedard |
| 2011/0224804 A1 | 9/2011 | Clausen et al. |
| 2011/0245931 A1 | 10/2011 | Clausen et al. |
| 2012/0016492 A1 | 1/2012 | Clausen |
| 2012/0191221 A1 | 7/2012 | Bedard et al. |
| 2012/0232672 A1 | 9/2012 | Ragnarsdottir et al. |
| 2013/0035769 A1 | 2/2013 | Bedard et al. |
| 2013/0297041 A1 | 11/2013 | Bedard et al. |

FOREIGN PATENT DOCUMENTS

| | | |
|---|---|---|
| CN | 1215614 | 5/1999 |
| CN | 2400072 Y | 10/2000 |
| DE | 3543291 | 6/1987 |
| DE | 3923056 | 1/1991 |
| DE | 3923057 | 1/1991 |
| DE | 4305213 | 8/1993 |
| DE | 4318901 | 1/1994 |
| DE | 4229330 | 3/1994 |
| DE | 195 21 464 A1 | 6/1995 |
| DE | 19521464 | 3/1997 |
| DE | 19 754 690 A | 7/1999 |
| EP | 0358056 | 3/1990 |
| EP | 0380060 | 8/1990 |
| EP | 503775 | 9/1992 |
| EP | 549855 | 9/1992 |
| EP | 628296 | 12/1994 |
| EP | 0 718 951 A | 6/1996 |
| EP | 0902547 A | 3/1999 |
| EP | 0 654 254 B1 | 9/1999 |
| EP | 957838 | 11/1999 |
| EP | 1066793 | 1/2001 |
| EP | 1125825 | 1/2001 |
| EP | 1 107 420 A | 6/2001 |
| EP | 1107420 A | 6/2001 |
| EP | 1 166 726 A1 | 1/2002 |
| EP | 1 169 982 A1 | 1/2002 |
| EP | 1340478 | 9/2003 |
| EP | 1613872 B1 | 4/2007 |
| EP | 1531767 B1 | 12/2008 |
| FR | 2 293 185 | 7/1976 |
| FR | 2623086 | 5/1989 |
| FR | 2 816 463 A | 5/2002 |
| GB | 2201260 | 8/1988 |
| GB | 2244006 | 11/1991 |
| GB | 2 260 495 A | 4/1993 |
| GB | 2301776 | 12/1996 |
| GB | 2 302 949 A | 2/1997 |
| GB | 2367753 | 8/1998 |
| GB | 2328160 | 2/1999 |
| GB | 2334891 | 9/1999 |
| GB | 2338653 | 12/1999 |
| GB | 2 343 848 A | 5/2000 |
| GB | 2 367 753 A | 4/2002 |
| JP | 59-32453 | 2/1984 |
| JP | 59-71747 | 4/1984 |
| JP | 60081530 | 5/1985 |
| JP | 59-189843 | 10/1985 |
| JP | 01-244748 | 9/1989 |
| JP | 3-181633 | 8/1991 |
| JP | 4-78337 | 3/1992 |
| JP | 05-123348 | 5/1993 |
| JP | 5-161668 | 6/1993 |
| JP | 7-24766 | 1/1995 |
| JP | 11056885 | 3/1999 |
| JP | 11000345 A2 | 6/1999 |
| JP | 11-215793 | 8/1999 |
| JP | 2001-1277175 | 10/2001 |
| JP | 2002-191654 A | 7/2002 |
| JP | 2005-500 | 1/2005 |
| KR | 2002/0041137 | 6/2002 |
| SU | 1447366 | 12/1988 |
| SU | 1731210 | 5/1992 |
| WO | WO 93/24080 A1 | 12/1993 |
| WO | WO 94/06374 | 3/1994 |
| WO | WO 94/09727 | 5/1994 |
| WO | WO 95/26171 A1 | 10/1995 |
| WO | WO 96/39110 | 12/1996 |
| WO | WO 96/41598 | 12/1996 |

(56) References Cited

FOREIGN PATENT DOCUMENTS

| | | |
|---|---|---|
| WO | WO 96/41599 | 12/1996 |
| WO | WO 97/00661 A | 1/1997 |
| WO | WO 97/00661 A1 | 1/1997 |
| WO | WO 97/27822 | 8/1997 |
| WO | WO 98/25552 | 6/1998 |
| WO | WO 98/38951 | 9/1998 |
| WO | WO 98/38951 A1 | 9/1998 |
| WO | WO 99/00075 | 1/1999 |
| WO | WO 99/08621 | 2/1999 |
| WO | WO 99/08621 A2 | 2/1999 |
| WO | WO 99/11206 | 3/1999 |
| WO | WO 99/05991 | 6/1999 |
| WO | WO 99/29272 | 6/1999 |
| WO | WO 99/44547 A1 | 9/1999 |
| WO | WO 99/55261 | 11/1999 |
| WO | WO 00/27318 A | 5/2000 |
| WO | WO 00/30572 | 6/2000 |
| WO | WO 00/30572 A1 | 6/2000 |
| WO | WO 00/38599 A1 | 7/2000 |
| WO | WO 00/71061 | 11/2000 |
| WO | WO 01/17466 A2 | 3/2001 |
| WO | WO 01/50986 A | 7/2001 |
| WO | WO 01/54630 | 8/2001 |
| WO | WO 01/72245 | 10/2001 |
| WO | WO 02/080825 | 10/2002 |
| WO | WO 03/003953 | 1/2003 |
| WO | WO 03/086245 A2 | 10/2003 |
| WO | WO 03/088373 A | 10/2003 |
| WO | WO 2004/017871 | 3/2004 |
| WO | WO 2004/017872 | 3/2004 |
| WO | WO 2004/017873 | 3/2004 |
| WO | WO 2004/092606 | 10/2004 |
| WO | WO 2005/041819 A2 | 5/2005 |
| WO | WO 2005/048887 | 6/2005 |
| WO | WO 2005/051248 | 6/2005 |
| WO | WO 2005/079172 A | 9/2005 |
| WO | WO 2005/079712 | 9/2005 |
| WO | WO 2008/080231 | 7/2008 |
| WO | WO 2008/080232 A1 | 7/2008 |
| WO | WO 2008/080233 A1 | 7/2008 |
| WO | WO 2008/080234 A1 | 7/2008 |
| WO | WO 2008/086629 A1 | 7/2008 |

OTHER PUBLICATIONS

Copes, Bionic Ankle: The Most Significant Development in Ankle Prosthetics in Over a Half Century, 1985, 3 pages, USA.

Proteor, Assembly and Adjustment Instructions for 1P50-R, pp. 1-21. Assembly and Adjustment Instructions for 1P50-R; Proteor; Publication No. 1P5099-R-09/04.

Blumentritt, Siegmar, Ph.D., et al.; Design Principles, Biomedical Data and Clinical Experience With a Polycentric Knee Offering Controlled Stance Phase Knee Flexion: A Preliminary Report, 1997, Journal of Prothetics and Orthotics, vol. 9, No. 1, 18-24.

Dietl, H., et al.; Der Einsatz von Elektronik Bei Prothesen Zur Versorgung Der Unterenextremitaet, Medizinisch Orthopadische Technik, Tentner Verlag. Stuttgart, DE, vol. 117, No. 1, Jan. 1997, pp. 31-35.

Elliott, Scott B.; "MR Microprocessor-Controlled Swing and Stance," Presentation to American Academy of Orthotists & Prosthetists (Feb. 4, 2004).

Herr, et al., "User-adaptive control of a magnetorheological prosthetic knee", Industrial Robot: an International Journal, vol. 30, No. 1, (2003) pp. 42-55.

Herr, Hugh, Presentation at "Experiencing the Frontiers of Biomedical Technology," (Mar. 10-11, 2003).

Kirsner, Scott, "A Step in the Right Direction Biomedical Horizons Expanding," Boston Globe (Mar. 17, 2003).

Lelas, et al., Hydraulic versus Magnetorheological-based Electronic Knee Protheses: A Clinical Comparison, Harvard Medical School, Dept.. of Phys. Med. and Rehab., Boston, MA pp. 1-16.

Otto Bock Orthopadische Industrie, C-LEG a new dimension in amputee mobility, Otto Bock Data Sheet 1997.

Otto Bock Orthopadische Industrie, The Electronic C-Leg compact Leg Prosthesis System, Instructions for Use; 2002.

Otto Bock, "The Electronic C-Leg Knee Joint System, Instructions for Use"; Published 2002.

Popovik, D., et al.; Optimal Control for an Above-Knee Prosthesis With Two Degrees of Freedom, 1995, pp. 89-98, J. Biomechanics, vol. 28, No. 1.

State-Of-The Art Prosthetic Leg Incorporates Magneto-Rheological Technology, Medical Product Manufacturing News, p. 42, Nov. 2000.

Van der Loos, H.F.M., et al. ProVAR Assistive Robot System Architecture ; Proceedings of the 1999 IEEE International Conference on Robotics & Automation; Detroit, Michigan, May 1999.

Wilkenfeld, Ari Ph.D., et al.; An Auto-Adaptive External Knee Prosthesis, Artificial Intelligence Laboratory, MIT, Cambridge, Massachusetts, 3 pages, Sep. 2000.

Wilkenfeld, Ari, Ph.D.; Biologically inspired autoadaptive control of a knee prosthesis, Dissertation Abstract, MIT, Cambridge, Massachusetts, 1 page, Sep. 2000.

U.S. Appl. No. 11/219,317, filed Sep. 1, 2005, published as 2007/0156252, including its ongoing prosecution history, including without limitation Office Actions, Amendments, Remarks, and any other potentially relevant documents.

U.S. Appl. No. 11/367,048, filed Mar. 1, 2006, published as 2006.0224247, including its ongoing prosecution history, including without limitation Office Actions, Amendments, Remarks, and any other potentially relevant documents.

U.S. Appl. No. 11/355,058, filed Feb. 15, 2006, published as 2006/0184252, including its ongoing prosecution history, including without limitation Office Actions, Amendments, Remarks, and any other potentially relevant documents.

U.S. Appl. No. 11/123,870, filed May 6, 2005, published as 2006/0136072, including its ongoing prosecution history, including without limitation Office Actions, Amendments, Remarks, and any other potentially relevant documents.

U.S. Appl. No. 11/512,645, filed Aug. 30, 2006, published as 2007/0050047, including its ongoing prosecution history, including without limitation Office Actions, Amendments, Remarks, and any other potentially relevant documents.

U.S. Appl. No. 11/355,047, filed Feb. 15, 2006, published as 2006/0184280, including its ongoing prosecution history, including without limitation Office Actions, Amendments, Remarks, and any other potentially relevant documents.

U.S. Appl. No. 11/289,038, filed Nov. 29, 2005, published as 2006/0122711, including its ongoing prosecution history, including without limitation Office Actions, Amendments, Remarks, and any other potentially relevant documents.

U.S. Appl. No. 12/815,166, filed Jun. 14, 2010, published as 2010/0262260, including its ongoing prosecution history, including without limitation Office Actions, Amendments, Remarks, and any other potentially relevant documents.

U.S. Appl. No. 10/600,725, filed Jun. 20, 2003, published as 2004/0049290, including its ongoing prosecution history, including without limitation Office Actions, Amendments, Remarks, and any other potentially relevant documents.

U.S. Appl. No. 11/270,684, filed Nov. 9, 2005, published as 2006/0122710, including its ongoing prosecution history, including without limitation Office Actions, Amendments, Remarks, and any other potentially relevant documents.

U.S. Appl. No. 11/881,964, filed Jul. 31, 2007, published as 2008/0046096, including its ongoing prosecution history, including without limitation Office Actions, Amendments, Remarks, and any other potentially relevant documents.

U.S. Appl. No. 11/891,098, filed Aug. 9, 2007, published as 2008/0058959, including its ongoing prosecution history, including without limitation Office Actions, Amendments, Remarks, and any other potentially relevant documents.

U.S. Appl. No. 12/160,727, filed Jan. 7, 2008, published as 2009/0299480, including its ongoing prosecution history, including without limitation Office Actions, Amendments, Remarks, and any other potentially relevant documents.

Proteor, Assembly and Adjustment Instructions for 1P5O-R; Publication No. 1P5099-R-09/04.

(56) References Cited

OTHER PUBLICATIONS

U.S. Appl. No. 12/692,438, filed Jan. 22, 2010, published as 2010/0185124, including its ongoing prosecution history, including without limitation Office Actions, Amendments, Remarks, and any other potentially relevant documents.
U.S. Appl. No. 11/218,923, filed Sep. 1, 2005, Clausen et al.
U.S. Appl. No. 11/219,317, filed Sep. 1, 2005, Jonsson, et al.
U.S. Appl. No. 11/367,048, filed Mar. 1, 2006, Clausen et al.
U.S. Appl. No. 11/367,049, filed Mar. 1, 2006, Clausen et al.
Advanced Materials & Processes, Sep. 2003, vol. 9, Issue 161, pp. 29-30, 3 pages.
Assembly and Adjustment Instructions for 1P5O-R; Proteor; Publication No. 1P5099-R-09/04.
Au S K et al., "An EMG-Position Controlled System for an Active Ankle-Foot Prosthesis: An Initial Experimental Study" Rehabilitation Robotics, 2005. ICORR 2005., 9th International Conference on Chicago, IL, USA Jun. 28—Jul. 1, 2005, Piscataway, NJ, IEEE, Jun. 28, 2005, pp. 375-379, XP008078417.
Examiner's First Report in Australian Patent Application No. 2003236750.
Blaya, J. A., et al., "Adaptive Control of a Variable-Impedance Ankle-Foot Orthosis to Assist Drop-Foot Gait" IEEE Transactions on Neural Systems and Rehabilitation Engineering, vol. 12, No. 1, Mar. 2004, pp. 24-31.
Carlson, J. David, What Makes a Good MR Fluid?, 8th International Conference on Electrorheological (ER) Fluids and Magnetorheological (MR) Suspensions, Nice 7 pages, Jul. 9-13, 2001.
Mar. 21, 2007 Office Action for co-pending U.S. Appl. No. 11/057,391, filed Feb. 11, 2005.
Mar. 31, 2006 OA from co-pending U.S. Appl. No. 11/057,391, System and Method for Motion-Controlled Foot Unit, filed Feb. 11, 2005.
Aug. 16, 2007 Office Action fr co-pending U.S. Appl. No. 11/057,391, filed Feb. 11, 2005.
Sep. 27, 2006 Office Action from co-pending U.S. Appl. No. 11/057,391, filed Feb. 11, 2005.
International Preliminary Report on Patentability (IPRP) & Written Opinion, mailed Aug. 24, 2006, PCT/US/2005/004878, 12 pages. (Repetitive of Written Opinion mailed Aug. 19, 2005).
Office Action dated Feb. 6, 2006 in Chinese Patent Application No. 200580008119.2.
Office Action dated Jun. 3, 2009 in co-pending U.S. Appl. No. 12/117,633, filed May 8, 2008.
Response to Jun. 3, 2009 Office Action dated Jul. 17, 2009 in co-pending U.S. Appl. No. 12/117,633, filed May 8, 2008.
EPO-European Search Report, Mar. 2, 2004.
EPO-International Search Report, Dec. 5, 2003: PCT/CA03/00902.
EPO-International Search Report, Jun. 20, 2003: PCT/CA03/00937.
Ferris, D. P., et al., An Ankle-Foot Orthosis Powered by Artificial Pneumatic Muscles, Journal of Applied Biomechanics, May 21, 2005, pp. 189-197.
Flowers, et al., An Electrohydraulic Knee-Torque Controller for a Prosthesis Stimulator, pp. 308, Journal of Biomechanical Engineering: Transactions of the ASME, Feb. 1977.
Grimes, Donald L., An Active Multi-Mode Above-Knee Prosthesis Controller, Massachusetts Institute of Technology 1979, 158 pages, 1979.
H. Dietl & H. Bargehr, Der Einsatz von Elektronik bei Prothesen zur Versorgung der unteren Extremitat, Med. Orth. Tech., 1997, pp. 31-35, volume-issue 117, Gentner Verlag Stuttgart, Austria.
International Preliminary Report on Patentability for App. No. PCT/US2007/005292 dated Sep. 12, 2008.
International Preliminary Report on Patentability, mailed Dec. 21, 2006, in related International application No. PCT/US2005/015802,13 pp.
International Search Report and Written Opinion mailed Aug. 19, 2005, Appl. No. PCT/US2005/004878, 15 pages.
International Search Report and Written Opinion mailed May 11, 2007, International Application No. PCT/2006/0333658, 13 pages.
International Search Report and Written Opinion, mailed May 11, 2007, International Application No. PCT/2006/033917, 10 pages.
International Search Report and Written Opinion, mailed Nov. 21, 2006 in related International application No. PCT/US2005/015802, 21 pp.
Invitation to Pay Additional Fees and Partial International Search Report mailed Jul. 24, 2006 in counterpart International application PCT/US2005/015802, 9 pages.
Office Action in corresponding Japanese Patent Application No. 2001-555610, dated May 21, 2008, with English translation, 8 pp.
Office Action issued on Dec. 25, 2009 in Chinese Patent Application No. 200680011678.3 with English Translation.
OSSUR Academy, 2004 Course Descriptions, OSSUR North America, 16 pages.
Otto Bock, Modular Knee Joints, http://www.healthcare.ottobock.com/technical_orthopedics/beinprothesen/sites/knee.htm , printed from the internet on Jul. 10, 2002, 4 pages.
Otto Bock, Orthopadische Industrie GMBH & Co., C-Leg Fitting Statistics (Abstract), Mar. 2000, 4 pages.
Otto Bock, Quality for Life, Software C-Soft, Menu-driven setting of the C-Leg, 2004 1 page.
Otto, Judith, Prosthetic Knees: What's Currently New and Impressive?, The O&P Edge, http://www.oandp.com/edge/issues/articles/2003-10_03.sp, Oct. 2003, 4 pages.
Otto, Judith, Prosthetic Knees: What's on the Way?, The O&P Edge, http://www.oandp.com/edge/issues/articles/2003-10_02.asp, Oct. 2003, 4 pages.
Partial International Search, PCT Application No. US2006/033658, mailed Jan. 15, 2007, 2 pages.
PCT International Search Report and Written Opinion mailed Aug. 19, 2005, Appl. No. PCT/US2005/004878, 15 pages.
PCT International Search Report dated Dec. 28, 2006, Appl. No. PCT/US2005/005352.
Suga, T., et al., "Newly designed computer controlled knee-ankle-foot orthosis (Intelligent Orthosis)", Missing Prosthetics and Orthotics International, 1998, 22, 230-239.
Townsend M A et al., "Biomechanics and modeling of bipedal climbing and descending." Journal of Biomechanics 1976, vol. 9, No. 4, pp. 227-239, XP008078405.
U.S. Appl. No. 11/367,048, filed Mar. 1, 2006.
U.S. Appl. No. 11/367,049, filed Mar. 1, 2006.
Zamiska, Nicholas, Bionic Knee 'Learns' How to Walk, 1 page, The Wall Street Journal, Jul. 6, 2004.
U.S. Appl. No. 13/754,298, Clausen et al.
Abbas, et al., Neural Network Control of Functional Neuromuscular Stimulation Systems: Computer Stimulation Studies, 1995.
Kamiar Aminian et al., *Estimation of Speed and Incline of Walking Using Neural Network*, IEEE Transactions on Instrumentation and Measurement, vol. 44, No. 3, Jun. 1995, at 743.
Andrews, BIJ., et al., Hybrid FES Orthosis Incorporating Closed Loop Control and Sensory Feedback, *J. Biomed. Eng.* 1988, vol. 10, Apr., 189-195.
Bachmann, et al., Inertial and Magnetic Tracking of Limb Segment Orientation for Inserting Humans into Synthetic Environments, 2000.
Bar, A., et al., "Adaptive Microcomputer Control of an Artificial Knee in Level Walking," J. Biomechanical Eng., vol. 5, pp. 145-150, 1983.
Baten, Inertial Sensing in Ambulatory Back Load Estimation, 1996.
Blaya, Force-Controllable Ankle Foot Orthosis (AFO) to Assist Drop Foot Gait, Feb. 2003 (believed to be catalogued on or after Jul. 8, 2003.
Bogert, et al., A Method for Inverse Dynamic Analysis Using Accelerometry, 1995.
Bortz, A New Mathematical Formulation for Strapdown Inertial Navigation, 1971.
Bouten, A Triaxial Accelerometer and Portable Data Processing Unit for the Assessment of Daily Physical Activity, 1997.
Bouten, Carlifin V., et al., Assessment of Energy Expenditure for Physical Activity Using a Triaxial Accelerometer. *Med. Sci. Sports Exerc.*, vol. 26, No. 12, pp. 151-1523, 1994.
Crago, et al., New Control Strategies for Neuroprosthetic Systems, 1996.

(56) References Cited

OTHER PUBLICATIONS

Dai R, et al., Application of Tilt Sensors in Functional Electrical Stimulation. IEEE Trans. Rehab. Eng. 1996; 4(2):63-71.
Fisekovic, et al., New Controller for Functional Electrical Stimulation Systems, 2000.
Foerster, et al., Detection of Posture and Motion by Accelerometry—A Validation Study in Ambulatory Monitoring, 1999.
Foxlin, et al., Miniature 6-DOF Inertial System for Tracking HMDs, 1998.
Fujita, K. et al., Joint Angle Control with Command Filter for Human Ankle Movement Using Functional Electrical Stimulation, Proceedings of the 9th Annual Conference of the IEEE Engineering in Medicine and Biology Society, Nov. 13-16, 1987.
Gelat, Thierry et al., Adaptation of the gait initiation process for stepping on to a new level using a single step. Exp Brain Res(2000) 133-538-546, Jun. 21, 2000, (9 pages).
Graps, A., An Introduction to Wavelets, IEEE Computational Science & Engineering, 1995.
Gronqvist, Raoul et al., Human-centered approaches in slipperiness measurement, Ergonomics, Oct. 20, 2001, vol. 44, Issue 13, pp. 1167-1199 (32 pages).
Hanafusa et al., "A Robot Hand with Elastic Fingers and Its Application to Assembly Process," pp. 337-359, Robot Motion, Brady et al., MIT Press, Cambridge, MA, 1982.
Hanson, James P. et al., Predicting slips and falls considering required and available friction, Ergonomics, 1999, vol. 42, Issue 12, pp. 1619-1633 (15 pages).
Hashimoto et al., "An instrumented compliant wrist using a parallel mechanism," Japan/USA Symposium on Flexible Automation, vol. 1, pp. 741-744, ASME, 1992.
Hayes, W.C., et al., Leg Motion Analysis During Gait by Multiaxial Accelerometry: Theoretical Foundations and Preliminary Validations. *Journal of Biomechanical Engineering*, vol. 105, Aug. 1983, p. 283-289.
Herr, et al., Patient-Adaptive Prosthetic and Orthotic Leg Systems, 12th Nordic Baltic Conference on Biomedical Engineering and Medical Physics, Proceedings of the International Federation for Medical & Biological Engineering, 2002.
Heyn, Andreas, et al., The Kinematics of the Swing Phase Obtained From Accelerometer and Gyroscope Measurements, *18th Annual International Conference of the IEEE Engineering in Medicine and Biology Society*, Amsterdam 1996, pp. 463-464.
Hill, Stephen W. et al., Altered kinetic strategy for the control of swing limb elevation over obstacles in unilateral below-knee amputee gait, Journal of Biomechanics, 1999, vol. 32, pp. 545-549 (5 pages).
Howard, "Joint and Actuator Design for Enhanced Stability in Robotic Force Control," Ph.D. thesis, Massachusetts Inst. of Technology, Dept. of Aeronautics and Astronautics, 1990.
Jones, S. F. et al., The gait initiation process in unilateral lower-limb amputees when stepping up and stepping down to a new level, Clinical Biomechanics, 2005, vol. 20, pp. 405-413 (9 pages).
Jonic, et al., Three Machine Learning Techniques for Automatic Determination of Rules to Control Locomotion, 1999.
Kidder, Steven M., et al., A System for the Analysis of Foot and Ankle Kinematics During Gait. *EEE Transactions on Rehabilitation Engineering*, vol. 4, No. 1, Mar. 1996.
Kirkwood, et al., Automatic Detection of Gait Events: A Case Study Using Inductive Learning Techniques, 1989.
Kooij, et al., A Multisensory Integration Model of Human Stance Control, 1998.
Kostov, et al., Machine Learning in Control of Functional Electrical Stimulation Systems for Locomotion, 1995.
Kuster, M., et al., Kinematic and kinetic comparison of downhill and level walking, Clinical Biomechanics, 1995, vol. 10, Issue 2, pp. 79-84 (6 pages).
LaFortune, Mario A., Three Dimensional Acceleration of the Tibia During Walking and Running. *J. Biomechanics* vol. 24, No. 10, pp. 877-886, 1991.

Lee, S., Activity and Location Recognition Using Wearable Sensors, Pervasive Computing, IEEE, 2002.
Light, L.H., et al., Skeletal Transients on Heel Strike in Normal Walking with Different Footwear, Biomechanics, vol. 13, 1980, pp. 477-480.
Luinge, H.J., Inertial Sensing of Movement. Doctoral Thesis, Twente University Press, Enschede, Netherlands (2002) pp. 9-13.
Martens, W., *Exploring Information Content and Some Application of Body Mounted Piezo-Resistive Accelerometers*, Phy Vision b.v., Gemert, The Netherlands.
Mayagoitia, Ruth E., et al., Accelerometer and Rate Gyroscope Measurement of Kinematics: An Inexpensive Alternative to Optical Motion Analysis Systems. *Journal of Biomechanics* 35 (2002) pp. 537-542.
Michel, V. et al., The strategies to regulate and to modulate the propulsive forces during gait initiation in lower limb amputees, Exp Brain Res, May 27, 2004, vol. 158, pp. 356-365 (10 pages).
Moe-Nilssen, A New Method for Evaluating Motor Control in Gait Under Real-Life Environmental Conditions, Parts 1—The instrument; Part 2: Gait Analysis, 1997.
Morris, J.R. W., Accelerometry—Technique for the Measurement of Human Body Movements, *J. Biomechanis*, 1973, vol. 6, pp. 729-736.
Moseley, Anne M. et al., High- and low-ankle flexibility and motor task performance, Gait and Posture, 2003, vol. 18, pp. 73-80 (8 pages).
"MT9 Inertial 3D Motion Tracker," Xsens Technologies B.Y., available at http://www.xsens.com/download/MT9_brochure.pdf (at least as early as Oct. 2004), printed Jul. 20, 2006, (2 pages).
Murray, M. Pat, et al. Walking Patterns of Normal Men, The Journal of Bone and Joint Surgery, vol. 46-A, No. 2, Mar. 1964.
Nadeau, S. et al., Frontal and sagittal plane analyses of the stair climbing task in healthy adults aged over 40 years: what are the challenges compared to level walking?, Clinical Biomechanics, 2003, vol. 18, pp. 950-959 (10 pages).
A. Nakagawa, Intelligent Knee Mechanism and the Possibility to Apply the Principle to the Other Joints, Engineering in Medicine and Biology Society, Proceedings of the 20th Annual International Conference of the IEEE, vol. 20, No. 5, Dec. 1998, at 2282.
Otto Bock's C-Leg, see http://web.archive.org/web/20040215152410/http:/www.ottobockus.com/products/lower_limb_prosthetics/c-leg.asp.
Perry, Jacquelin, MD, Gait Analysis: Normal and Pathological Function, Ch. 4, pp. 51-53, 85-87, 1992.
Petrofsky, Jerrold S., et. al., Feedback Control System for Walking in Man. *Comput. Biol. Med*. vol. 14, No. 2, pp. 135-149, 1984.
Pfeffer et al., "Experiments with a Dual-Armed, Cooperative, Flexible-Drivetrain Robot System," Proc. 1993 IEEE Int. Conf. on Robotics & Automation, vol. 3, pp. 601-608, May 5, 1993.
Dejan Popovic et al., Control Aspects of Active Above-Knee Prosthesis, International Journal of Man-Machine Studies, vol. 35, Issue 6, Dec. 1991, at 751.
Powers, Christopher M. et al., Stair ambulation in persons with transtibial amputation: An analysis of the Seattle LightFootTM, Journal of Rehabilitation Research and Development, Jan. 1997, vol. 34, Issue 1, pp. 9-18 (10 pages).
Rao, Sreesha S. et al., Segment Velocities in Normal and Transtibial Amputees: Prosthetic Design Implications, IEEE Transactions on Rehabilitation Engineering, Jun. 1998, vol. 6, Issue 2, pp. 219-226 (8 pages).
Redfern, Mark S. et al., Biomechanics of descending ramps, Gait and Posture, 1997, vol. 6, pp. 119-125 (7 pages).
Reiner, Robert et al., Stair ascent and descent at different inclinations, Gait and Posture, 2002, vol. 15, pp. 32-44 (13 pages).
Reitman, J. S., et al., Gait Analysis in Prosthetics: Opinions, Ideas, and Conclusions, Prosthetics and Orthotics International, 2002, 26, pp. 50-57.
Robinson, David W. et al., *Series Elastic Actuator Development for a Biomimetic Walking Robot*, MIT Leg Laboratory, 1999.
Robinson, David William, *Design and Analysis of Series Elasticity in Closed-Loop Actuator Force Control*, MIT Department of Mechanical Engineering, Jun. 1996.
Sekine, et al., Classification of Waist-Acceleration Signals in a Continuous Walking Record, 2000.

(56) References Cited

OTHER PUBLICATIONS

Sin S. W., et al., Significance of Non-Level Walking on Transtibial Prosthesis Fitting with Particular Reference to the Effects of Anterior-Posterior Alignment, Journal of Rehabilitation Research and Development vol. 38 No. 1, Jan./Feb. 2001, pp. 1-6.

Smidt, G.L., et al., An Automated Accelerometry System for Gait Analysis, *J. Biomechanics*. 1977, vol. 10, pp. 367-375.

Sugano et al., "Force Control of the Robot Finger Joint equipped with Mechanical Compliance Adjuster," Proc. 1992 IEEE/RSJ Int. Conf. on Intell. Robots & Sys., pp. 2005-2013, Jul. 1992.

Thakkar, Sneha, "Energy Economy Gait Analysis of an Autoadaptive Prosthetic Knee", Master's Thesis submitted to the Dept. of Electrical Engineering and Computer Science, MIT (2002) pp. 1-58.

R. Tomovic et al., *A Finite State Approach to the Synthesis of Bioengineering Control Systems*, IEEE Transactions on Human Factors in Electronics, vol. HFE-7, No. 2, Jun. 1966.

Tong, et al., Virtual Artificial Sensor Technique for Functional Electrical Stimulation, 1998.

Tong, Kaiyu and Malcolm H. Granat, *A Practical Gait Analysis System Using Gyroscopes*, Medical Engineering & Physics, vol. 21, No. 2, Mar. 1999, pp. 87-94.

U.S. Appl. No. 60/371,974 to Martin, filed Apr. 12, 2002.

Van der Loos, H.F.M., et al., "ProVAR Assistive Robot System Architecture", Proceedings of the 1999 IEEE International Conference on Robotics & Automation; Detroit, Michigan, May 1999, pp. 741-46.

Peter H. Veltink et al. (1993), The Feasibility of Posture and Movement Detection by Accelerometry, in 15th Annual International Conference of the IEEE Engineering in Medicine and Biology Society, Oct. 28-31, 1993, San Diego, CA, 1230-1231.

Veltink, et al., Detection of Static and Dynamic Activities Using Uniaxial Accelerometers, 1996.

Wilkenfeld, Ari Ph.D.; An Auto-Adaptive External Knee Prosthesis, Artificial Intelligence Laboratory, MIT, Cambridge, Massachusetts, 3 pages, Sep. 2000.

Wilkenfeld, Ari Ph.D.; Biologically inspired autoadaptive control of a knee prosthesis, Dissertation Abstract, MIT, Cambridge, Massachusetts, (1 page), Sep. 2000.

Willemsen, A. TH. M., et al., Real-Time Gait Assessment Utilizing a New Way of Accelerometry. *J. Biomechanics* vol. 23, No. 8, pp. 859-863, 1990.

Willemsen, Antoon Th. M., et al., Automatic Stance-Swing Phase Detection from Accelerometer Data for Peroneal Nerve Stimulation. *IEEE Trasnactions on Biomedical Engineering*, vol. 37, No. 12, Dec. 1990, pp. 1201-1208.

Williamson, Matthew M., *Series Elastic Actuators*, Massachusetts Institute of Technology Artificial Intelligence Laboratory, A.I. Technical Report No. 1524, Jan. 1995.

Woodward, M I, et al., Skeletal Accelerations Measured During Different Exercises. *Proceedings of the Institution of Mechanical Engineers*, Part H: Journal of Engineering Medicine 1993 207:79, DOI: 10.1243/PIME_PROC_1993_207_{1 274}_02.

Wu, Ge, The Study of Kinematic Transients in Locomotion Using the Integrated Kinematic Sensor, IEEE Transactions on Rehabilitation Engineering, vol. 4, No. 3, Sep. 1996, pp. 193-200.

Zamiska, Nicholas, Bionic Knee 'Learns' How to Walk, (1 page), The Wall Street Journal, Jul. 6, 2004.

Complaint for Patent Infringement filed Nov. 15, 2011, *Össur hf v. iWalk, Inc.* (involving U.S. Pat. No. 7,431,737 and 7,896,927), Case No. SACV11-01759 AN, 85 pages.

Defendant iWalk's Answer and Counterclaim to Plaintiff's Complaint for Patent Infringement filed Jan. 6, 2012, *Össur hf v. iWalk, Inc.* (involving U.S. Pat. Nos. 7,431,737 and 7,896,927), Case No. SACV-01759 AN, 95 pages.

Defendant iWalk's First Amended Answer and Counterclaim to Plaintiffs' Complaint for Patent Infringement filed Jan. 26, 2012, *Össur hf v. iWalk, Inc.* (involving U.S. Pat. Nos. 7,431,737 and 7,896,927), Case No. SACV-01759 AN, 20 pages.

Defendant iWalk's Amended Answer and Counterclaim filed Feb. 3, 2012, *Össur hf v. iWalk, Inc.* (involving U.S. Pat. Nos. 7,431,737 and 7,896,927), Case No. SACV-01759 JST, 94 pages.

Ossur's Reply to iWalk's Amended Counterclaims and Demand for Jury Trial filed Feb. 9, 2012, *Össur hf v. iWalk, Inc.* (involving U.S. Pat. Nos. 7,431,737 and 7,896,927), Case No. SACV11-01759 JST, 8 pages.

Memorandum of Points and Authorities in Support of Defendant iWalk's Motion to Transfer Venue, filed Apr. 2, 2012, *Össur hf v. iWalk, Inc.* (involving U.S. Pat. Nos. 7,431,737 and 7,896,927), Case No. SACV-01759 JST, 19 pages.

Defendant iWalk's Reply in Support of Its Motion to Transfer Venue, filed Apr. 23, 2012, *Össur hf v. iWalk, Inc.* (involving U.S. Pat. Nos. 7,431,737 and 7,896,927), Case No. SACV 01759, 18 pages.

Redacted version of Plaintiff Ossur's Disclosure of Asserted Claims and Infringement Contentions, filed Jun. 11, 2012, *Össur hf v. iWalk, Inc.* (involving U.S. Pat. Nos. 7,431,737 and 7,896,927), Case No. SACV11-01759 JST (MLGx), 223 pages.

Plaintiff Ossur's Preliminary Proposed Claim Constructions, served Sep. 20, 2012, *Ossur hf v. iWalk, Inc.* (involving U.S. Pat. Nos. 7,431,737 and 7,896,927), Case No. SACV11-01759 JST (MLGx), 10 pages.

Ossur's Claim Construction and Prehearing Statement filed Oct. 1, 2012, *Össur hf v. iWalk, Inc.* (involving U.S. Pat. Nos. 7,431,737 and 7,896,927), Case No. 12-CV-11061-FDS, 17 pages.

Defendant iWalk's Preliminary Invalidity Contentions filed Nov. 30, 2012, *Össur hf v. iWalk, Inc.* (involving U.S. Pat. Nos. 7,431,737 and 7,896,927), Case No. 12-CV-11061 FDS, 157 pages.

Redacted version of Defendant iWalk's Preliminary Non-Infringement Contentions filed Nov. 30, 2012, *Össur hf v. iWalk, Inc.* (involving U.S. Pat. Nos. 7,431,737 and 7,896,927), Case No. 12-CV-11061 FDS, 20 pages.

Ossur's Identification of Claim Terms and Proposed Constructions served Feb. 1, 2013, *Össur hf v. iWalk, Inc.* (involving U.S. Pat. Nos. 7,431,737 and 7,896,927), Case No. SACV11-01759 JST (MLGx), 8 pages.

iWalk's Identification of Disputed Claim Terms and Proposed Constructions, served Feb. 1, 2013, *Össur hf v. iWalk, Inc.* (involving U.S. Pat. Nos. 7,431,737 and 7,896,927), Case No. SACV11-01759 JST (MLGx), 5 pages.

Ossur and iWalk's Disputed Claim Terms and Proposed Constructions, exchanged Feb. 5, 2013, *Össur hf v. iWalk, Inc.* (involving U.S. Pat. Nos. 7,431,737 and 7,896,927), Case No. SACV11-01759 JST (MLGx), 7 pages.

Ossur's Opening Claim Construction Brief filed Feb. 8, 2013, *Össur hf v. iWalk, Inc.* (involving U.S. Pat. Nos. 7,431,737 and 7,896,927), Case No. 12-CV-11061 FDS, 48 pages.

iWalk's Opening Claim Construction Brief filed Feb. 8, 2013, *Össur hf v. iWalk, Inc.* (involving U.S. Pat. Nos. 7,431,737 and 7,896,927), Case No. 12-CV-11061 FDS, 33 pages.

Ossur's Responsive Claim Construction Brief filed Feb. 19, 2013, *Össur hf v. iWalk, Inc.* (involving U.S. Pat. Nos. 7,431,737 and 7,896,927), Case No. 12-CV-11061 FDS, 23 pages.

iWalk's Responsive Claim Construction Brief filed Feb. 19, 2013, *Össur hf v. iWalk, Inc.* (involving U.S. Pat. Nos. 7,431,737 and 7,896,927), Case No. 12-CV-11061 FDS, 19 pages.

Declaration of Steven A. Gard, Ph.D., in Support of Ossur's Responsive Claim Construction Brief Regarding Purported Indefiniteness of Three Disputed Claim Terms, filed Feb. 19, 2013, *Össur hf v. iWalk, Inc.* (involving U.S. Pat. Nos. 7,431,737 and 7,896,927), Case No. 12-CV-11061 FDS, 47 pages.

iWalk's Markman Tutorial and Presentation, Feb. 25, 2013, *Össur hf v. iWalk, Inc.* (involving U.S. Pat. Nos. 7,431,737 and 7,896,927), Case No. 12-CV-11061 FDS, 94 pages.

Össur's Claim Construction Presentation, Feb. 25, 2013, *Össur hf v. iWalk, Inc.* (involving U.S. Pat. Nos. 7,431,737 and 7,896,927), Case No. 12-CV-11061 FDS, 81 pages.

Transcript of Markman Hearing held Feb. 25, 2013, *Össur hf v. iWalk, Inc.* (involving U.S. Pat. Nos. 7,431,737 and 7,896,927), Case No. 12-CV-11061 FDS, 120 pages.

Request for Ex Parte Reexamination of U.S. Patent No. 7,431,737 (without Appendices A2-A10), U.S. Appl. No. 90/012,731, filed Dec. 5, 2012.

Request for Ex Parte Reexamination of U.S. Patent No. 7,896,927 (without Appendices A1-A7), U.S. Appl. No. 90/012,732, filed Dec. 5, 2012.

(56) References Cited

OTHER PUBLICATIONS

Declaration of Diane Geraci dated Jun. 26, 2012, including Exhibits A, B, and C, submitted as Appendix A3 to the Request for Ex Parte Reexamination of U.S. Patent No. 7,431,737, filed Dec. 5, 2012 (Reference No. 267, above), and submitted as Appendix A5 to the Request for Ex Parte Reexamination of U.S. Patent No. 7,896,927, filed Dec. 5, 2012 (Reference No. 268, above).

Flowers, A Man-Interactive Simulator System for Above-Knee Prosthetics Studies, Aug. 1972.

Perry, Jacquelin, MD, Gait Analysis: Normal and Pathological Function, 1992.

Sowell, T.T., A Preliminary Clinical Evaluation of the Mauch Hydraulic Foot-Ankle System, 5 Prosthetics and Orthotics International 87 (1981).

Ossur's First Amended Preliminary Infringement Disclosures, served Jan. 2013, *Össur hf v. iWalk, Inc.* (involving U.S. Pat. Nos. 7,431,737 and 7,896,927), Case No. 12-CV-11061 FDS, 192 pages.

Memorandum and Order on Claim Construction, Aug. 8, 2013, *Össur hf v. iWalk, Inc.* (involving U.S. Pat. Nos. 7,431,737 and 7,896,927), Case No. 12-CV-11061 FDS, 51 pages.

Response to Office Action of Jun. 20, 2013 in the Ex Parte Reexamination of U.S. Patent No. 7,431,737, U.S. Appl. No. 90/012,731, filed Sep. 19, 2013.

Declaration of Steven A. Gard dated Sep. 19, 2013 in Ex Parte Reexamination of U.S. Patent No. 7,431,737, U.S. Appl. No. 90/012,731, with Exhibits 1, 2, 4, 5, and 6. Exhibit 3 is omitted as it is submitted separately as reference 13 in this Information Disclosure Statement.

Response to Office Action of Jun. 14, 2013 in the Ex Parte Reexamination of U.S. Patent No. 7,896,927, U.S. Appl. No. 90/012,732, filed Sep. 16, 2013.

Declaration of Steven A. Gard dated Sep. 13, 2013 in Ex Parte Reexamination of U.S. Patent No. 7,896,927, U.S. Appl. No. 90/012,732.

Office Action in the Ex Parte Reexamination of U.S. Patent No. 7,431,737, U.S. Appl. No. 90/012,731, dated Jun. 20, 2013.

Office Action in the Ex Parte Reexamination of U.S. Patent No. 7,896,927, U.S. Appl. No. 90/012,732, dated Jun. 14, 2013.

Office Action in the Ex Parte Reexamination of U.S. Patent No. 7,896,927, U.S. Appl. No. 90/012,732, dated Oct. 25, 2013.

Response to Office Action of Oct. 25, 2013 in the Ex Parte Reexamination of U.S. Patent No. 7,896,927, U.S. Appl No. 90/012,732, filed Dec. 23, 2013.

* cited by examiner

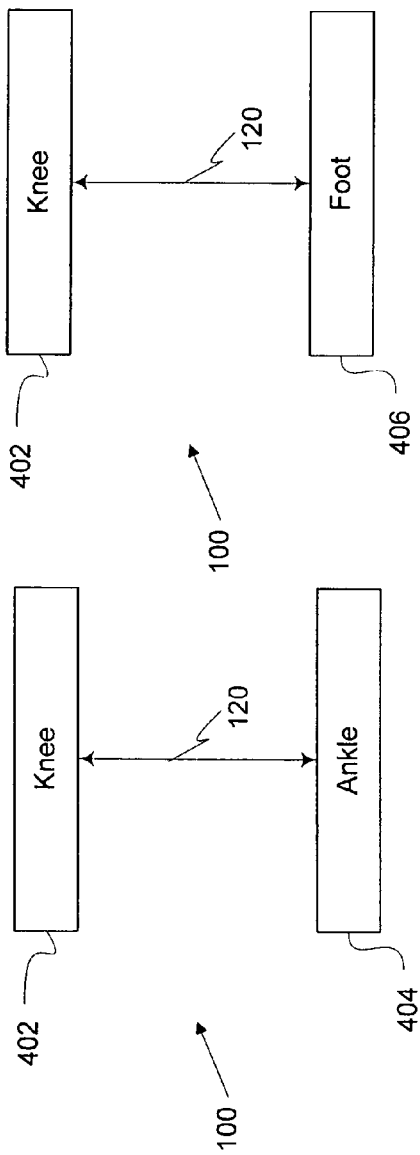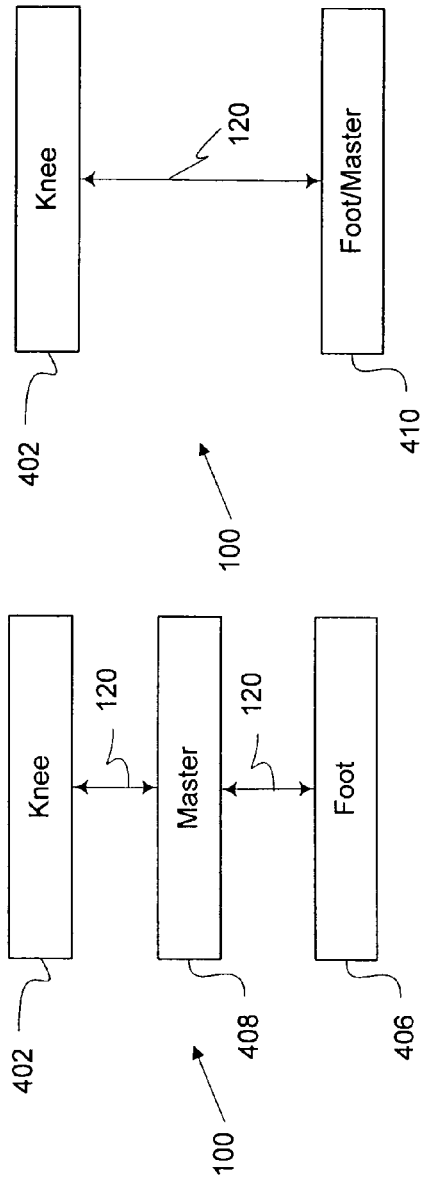

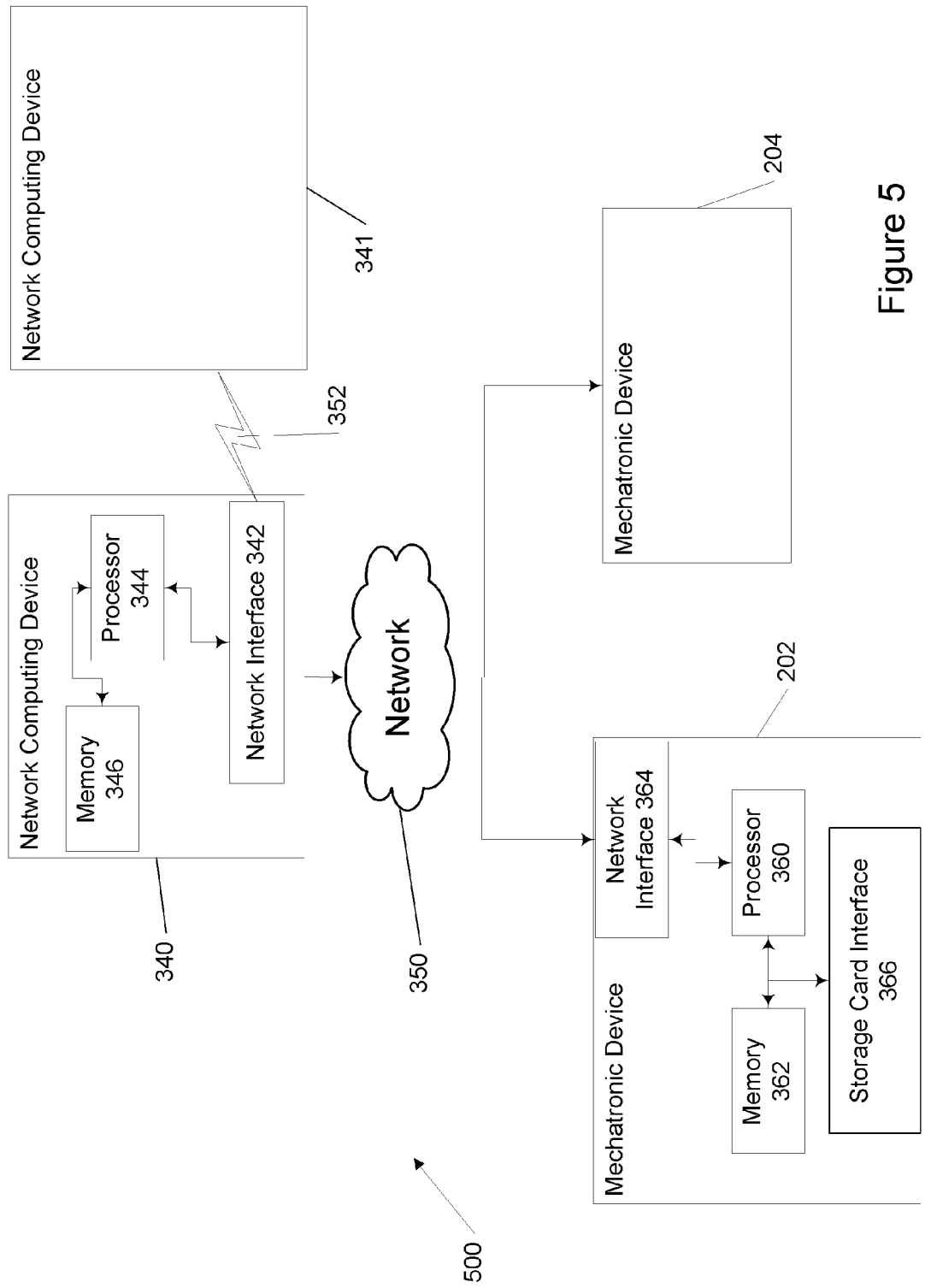

SYSTEM AND METHOD FOR DATA COMMUNICATION WITH A MECHATRONIC DEVICE

RELATED APPLICATIONS

This application claims the benefit of, and incorporates by reference in their entirety, U.S. Provisional Application No. 60/653,717, filed Feb. 16, 2005 and U.S. Provisional Application No. 60/679,953, filed May 10, 2005.

This application is also related to U.S. patent application Ser. No. 11/355,047 filed on even date and incorporated by reference its entirety.

BACKGROUND OF THE INVENTION

1. Field of the Invention

The present invention relates to prosthetic and orthotic limbs in general and, in addition, a system and method of configuring and synchronizing the adaptive control systems of prosthetic and orthotic devices on a patient.

2. Description of the Related Art

Prosthetic and orthotic devices, such as are attached to a human limb, have benefited from advances in electronics. Electronically controlled prosthetic or orthotic devices, which may be generally referred to as "mechatronic" devices, for example, prosthetic knees, can provide safer and more natural movement to patients who are equipped with such systems. However, advances in electronics appear to have outpaced the advances in control systems. Thus, control systems for prosthetic systems can benefit from intelligent architectures.

Further, the proliferation of electronic control systems for prosthetic and orthotic systems has created a need for systems and methods of synchronizing multiple devices which are worn by a single patient, e.g., a prosthetic knee and a prosthetic ankle. Operating in isolation from each other, multiple control systems may fail to provide the patient with stable, coordinated movement. In addition, independent configuration of multiple prosthetic devices can be inconvenient. Thus, it is desirable to have systems and methods of configuration, communication, and synchronization between such control systems. Further, it is desirable to have systems and methods of adding, replacing, or augmenting portions of the software in such control systems.

SUMMARY OF THE CERTAIN EMBODIMENTS

After considering this discussion, and particularly after reading the section entitled "Detailed Description of Certain Embodiments" one will understand how the features of this invention provide advantages that include providing a prosthetic or orthotic control system that provides more natural and comfortable movement to its users and enabling a more convenient and intuitive configuration, addition, replacement, or augmentation of control system software.

One embodiment is a system for controlling motion of a human limb. The system may include a plurality of mechatronic devices. Each of the plurality of mechatronic devices is in communication with at least one other of the plurality of mechatronic devices. At least one of the mechatronic devices controls an actuator. In one such embodiment, at least one of the plurality of mechatronic devices is configured to generate a control state for at least one other of the plurality of mechatronic devices based on the communicated data. In one embodiment, the communicated data is used to synchronize the mechatronic devices. In one embodiment, each of the mechatronic devices comprises an artificial joint. In one embodiment, at least one of the plurality of mechatronic devices comprises a prosthetic knee and at least one of the mechatronic devices comprises a prosthetic ankle.

Another embodiment is a mechatronic device for controlling motion of a human limb in cooperation with at least one other mechatronic device. The mechatronic device includes a communication interface configured to communicate data with the at least one other mechatronic device, a sensor configured to obtain a value indicative of at least one motion parameter of the limb; an actuator configured to affect at least one motion parameter of the mechatronic device, and a processor configured to activate the actuator based on the received communicated data and the at least one motion parameter value. In one embodiment, the communicated data may include the parameter value obtained from the sensor. In another embodiment, the communicated data may include state machine data received from the other mechatronic devices. In yet another embodiment, the communicated data may include configuration data received from the other mechatronic devices.

Another embodiment is a mechatronic device for controlling motion of a human limb in cooperation with at least one other mechatronic device. The mechatronic device includes a communication interface configured to communicate data with the at least one other mechatronic device, and a processor configured to generate a control state of the at least one other mechatronic device. The processor is further configured to communicate data associated with the control state through the communication interface. The mechatronic device further includes an actuator controlled by the processor so as to effectuate movement of the human limb. In another embodiment, the communicated data may include software that when executed by the processor is configured to affect the selection of the control state. In one embodiment, the communicated data includes data obtained by the at least one sensor of the other mechatronic device. In one embodiment, the communicated data includes configuration data obtained by the at least one sensor of the other mechatronic device. In one embodiment, the processor is further configured to determine at least one actuator control command based on the control state, and wherein the communicated data includes the at least one actuator control command.

Another embodiment is a method of synchronizing a first mechatronic device with a second mechatronic device. The method includes communicating data from the second mechatronic device to the first mechatronic device. The method further includes generating a control state in response to the received data. The method further includes controlling an actuator on the second mechatronic device based at least in part on the control state. In one embodiment, the method further includes generating a command to control an actuator of the second mechatronic device in response to the control state. In one embodiment, the method further includes generating a command to control an actuator of the first mechatronic device in response to the communicated data. In one embodiment, the received data includes sensor data received from the second mechatronic device. In another embodiment, the received data includes at least a portion of information indicative of the control state. In yet another embodiment, the received data includes computer software and the control state is performed at least partly by executing the computer software.

Another embodiment is a system for controlling motion of a device associated with a limb. The system includes a mechatronic device. The system further includes a sensor associated with a human limb which provides motion parameter data to the mechatronic device. The mechatronic device uses the motion parameter data for synchronization. In one embodiment, the sensor receives signals from the human nervous system. In one embodiment, the sensor receives signals from a sensor associated with a sound limb. In one embodiment, the motion parameter data is used for synchronization with another mechatronic device. In one such embodiment, the other mechatronic device provides motion parameter data to the mechatronic device.

One embodiment is a method of synchronizing a computing device with a a device associated with a limb. The method includes communicating data between the mechatronic system and the computing device, storing the data on the computing device, generating a control state on the mechatronic system in response to the data, and controlling an actuator on the second mechatronic system based at least in part on the control state.

Another embodiment is a mechatronic system attached to a human body. The device includes a sensor configured to provide data indicative of movement of the human body. An actuator is configured to control movement of at least a portion of the human body. A processor is configured to execute instructions configured to control the actuator based on the sensor data. A communication interface is configured to communicate data with a data source. The processor is further configured to receive at least a portion of the instructions from the data source. In one embodiment, the mechatronic system may include a separation of the processing, sensing, actuation, and communications in two or more mechatronic devices.

BRIEF DESCRIPTION OF THE DRAWINGS

FIG. 4A is a schematic block diagram of an exemplary embodiment of the system of FIG. 1F that includes a prosthetic knee and a prosthetic ankle.

FIG. 4B is a schematic block diagram of an exemplary embodiment of the system of FIG. 1F that includes a prosthetic knee and a prosthetic foot.

FIG. 4C is a schematic block diagram of another exemplary embodiment of the system of FIG. 1F that includes a prosthetic knee, a prosthetic foot, and a master device.

FIG. 4D is a schematic block diagram of another exemplary embodiment of the system of FIG. 1F that includes a prosthetic knee and a prosthetic foot in which the prosthetic foot includes one or more state machines for controlling both devices.

FIG. 5 is a block diagram illustrating one embodiment of a system including mechatronic devices in communication with personal and network computing devices.

DETAILED DESCRIPTION OF CERTAIN EMBODIMENTS

The following detailed description is directed to certain specific embodiments of the invention. However, the invention can be embodied in a multitude of different ways. In this description, reference is made to the drawings wherein like parts are designated with like numerals throughout.

The terms "prosthetic" and "prosthesis" as used herein are broad terms and are used in their ordinary sense and refer to, without limitation, any system, device or apparatus that may be used as an artificial substitute or support for a body part.

The term "orthotic" and "orthosis" as used herein are broad terms and are used in their ordinary sense and refer to, without limitation, any system, device or apparatus that may be used to support, align, prevent, protect, correct deformities of, immobilize, or improve the function of parts of the body, such as joints and/or limbs.

A device associated with a limb is any device that may be used to assist the limb in some function. For instance, a prosthetic device is a device associated with a limb. A prosthetic device may replace a portion of or the entire limb. Alternatively, an orthotic device is a device associated with a limb. An orthotic device, for instance, supports or aligns the limb. Additionally, other devices, such as articles of clothing or sporting goods equipment, may be devices associated with a limb. For instance, a shoe is a device associated with a limb because it assists the user of the shoe to use the foot, for example, to walk or run. Similarly, a ski boot is a device associated with a limb because it assists the user of the ski boot to use the foot, for example, to ski.

The term "mechatronic" as used herein is a broad term and is used in its ordinary sense and refer to, without limitation, any system, device or apparatus that includes an electronically controlled device associated with a limb, including a prosthetic or orthotic device. Such devices may include one or more of a sensor, an actuator, or processor.

The term "bionic" as used herein is a broad term and is used in its ordinary sense and refer to, without limitation, any system, device, or apparatus that includes an electronically controlled device integrated to replace or enhance anatomical structures or physiological processes. Bionic may also include electronic or mechanical smart structures or systems integrated to replace or enhance anatomical structures or physiological processes. For example, a bionic may include a mechatronic device such as prosthetic or orthotic.

Figure 1A:
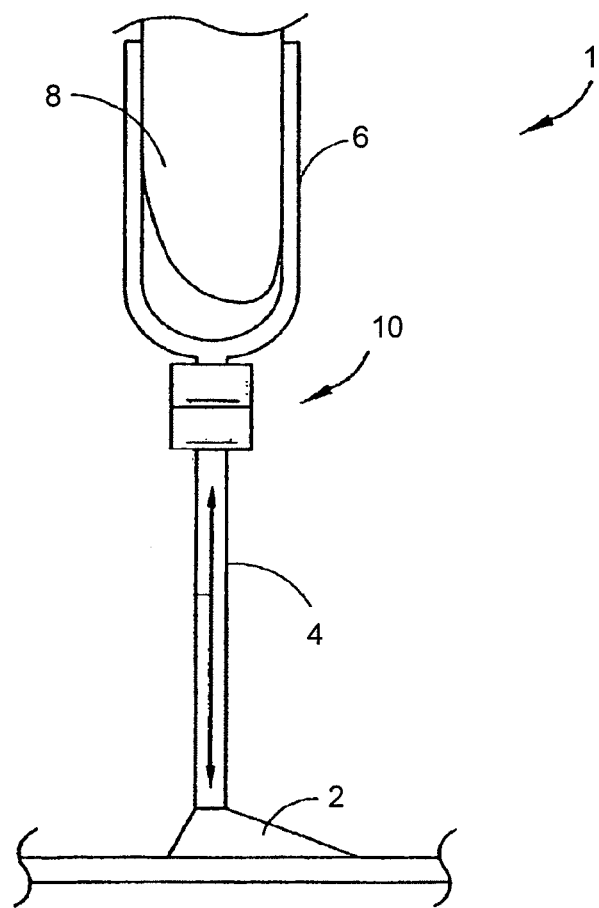
FIG. 1A is a simplified schematic view of a lower limb prosthetic assembly with an electronically controlled prosthetic knee illustrating features and advantages in accordance with an embodiment of the invention.
Figure 1B:
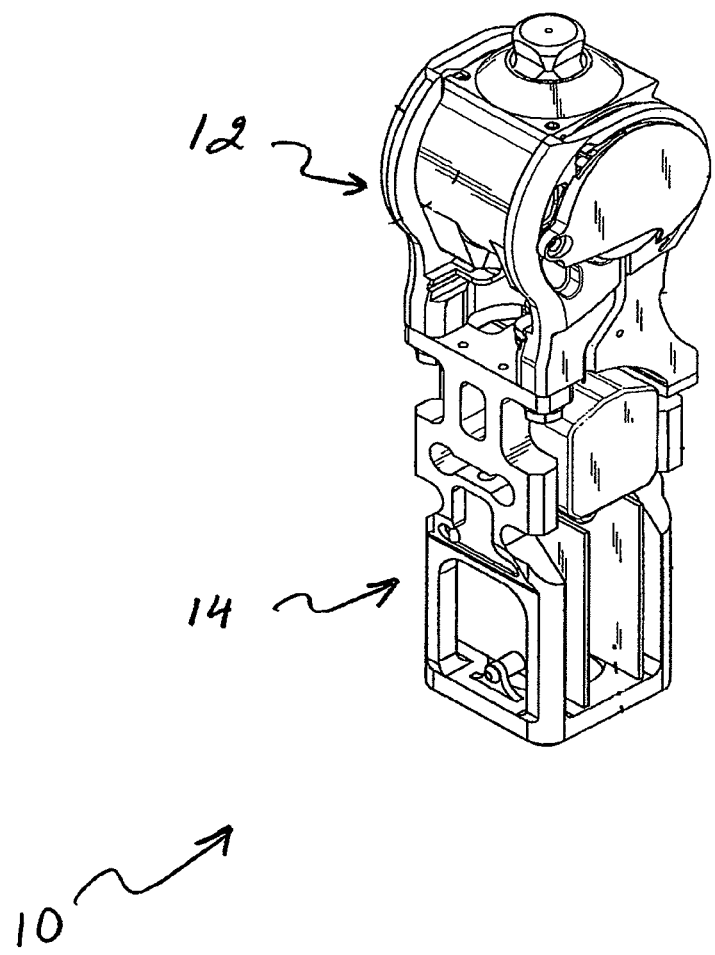
FIGS. 1B-1E are simplified perspective views of a prosthetic knee assembly illustrating features and advantages in accordance with an embodiment of the invention.
Figure 1C:
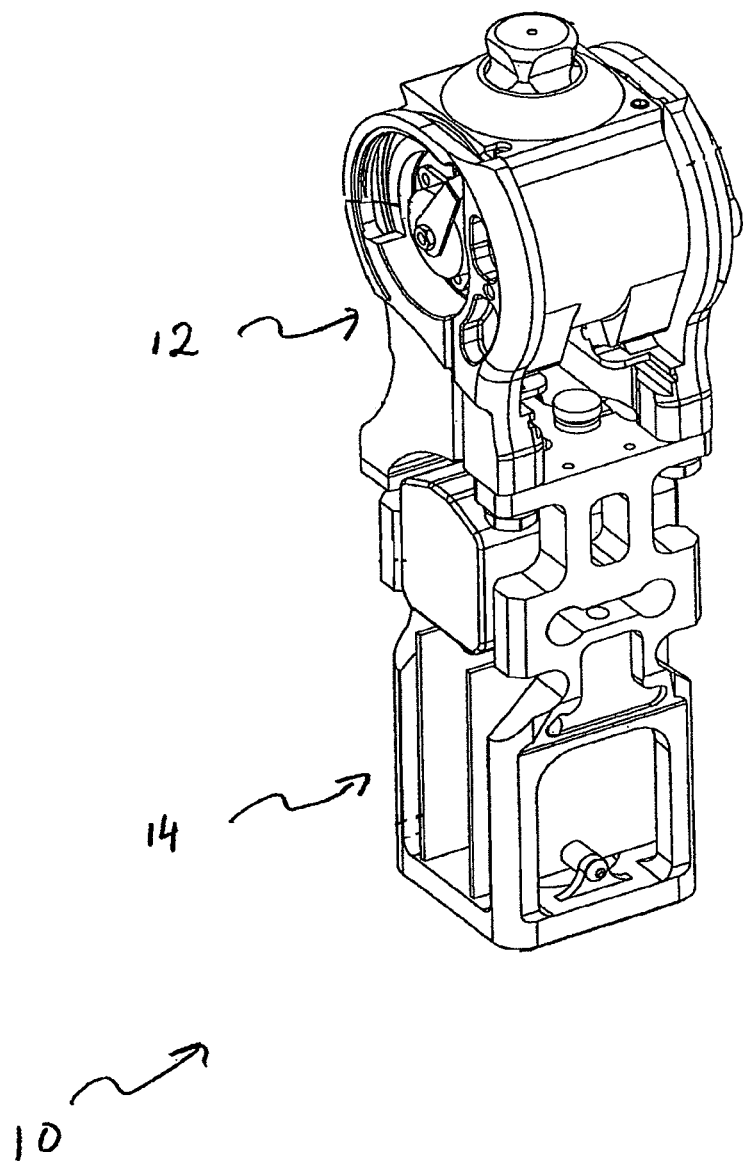
Figure 1D:
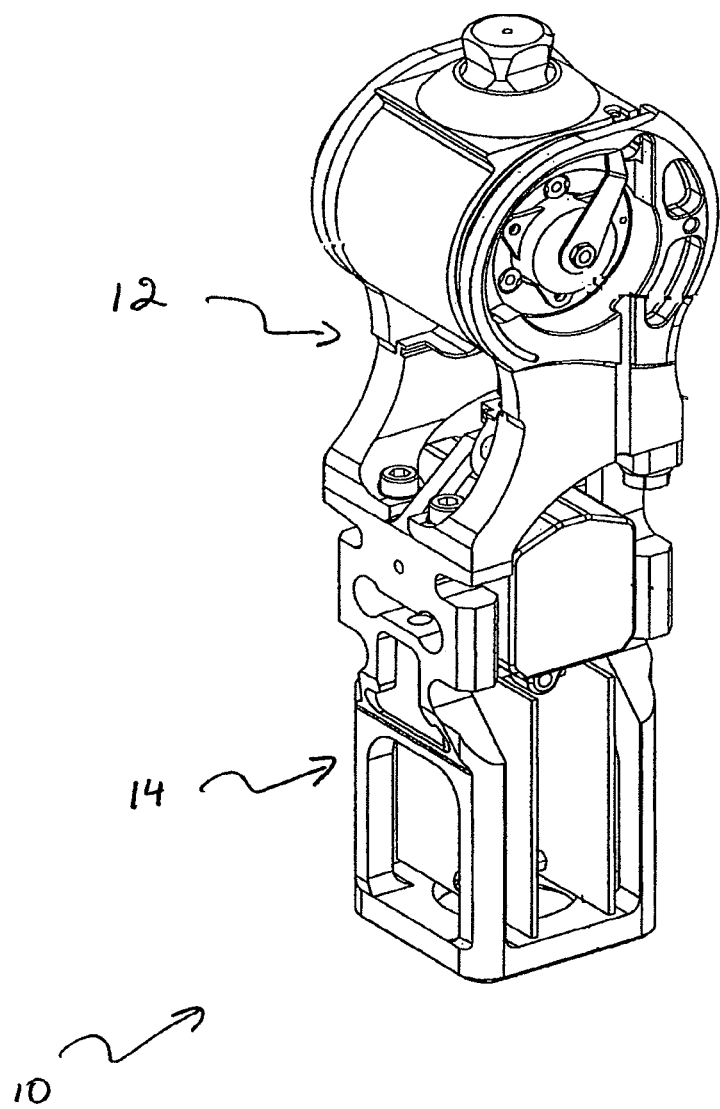
Figure 1E:
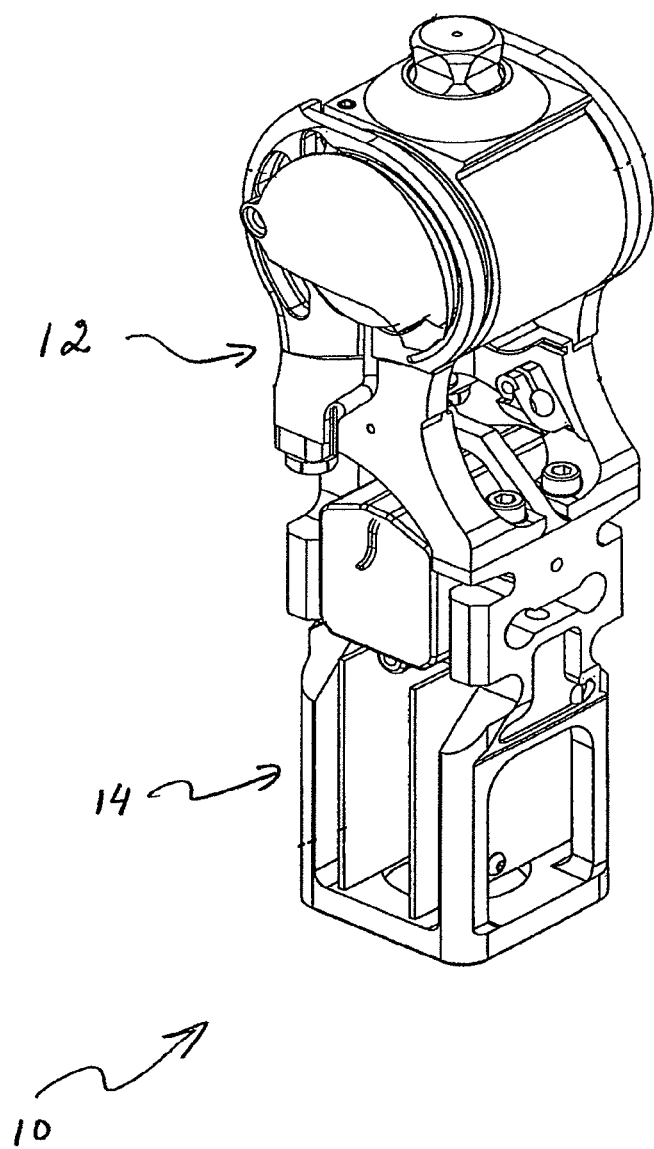

FIG. 1A is a schematic illustration of an embodiment of a lower limb prosthetic assembly, system or prosthesis 1 including an electronically controlled active knee prosthetic assembly, system or prosthesis 10. As described in greater detail later herein, advantageously, the knee prosthesis 10 provides resistive forces to substantially simulate the position and motion of a natural knee joint during ambulation and/or other locomotory or stationary activities performed by an amputee. The prosthetic or artificial knee 10 is desirably safe, reliable and generally comfortable to use by the amputee.

The prosthetic lower limb 1 further includes an artificial or prosthetic foot 2 coupled or mechanically connected to a pylon, tube, shaft or shank portion 4 that connects to a distal or bottom portion of the prosthetic knee 10 and a residual limb or stump socket 6 that connects to a top or proximal end of the prosthetic knee 10. The stump socket 6 receives a residual limb or femur portion 8 of the amputee. A suitable pylon or the like can also be provided between the stump socket 6 and the prosthetic knee 10, as needed or desired.

Embodiments of the invention van be practiced with a wide variety of prosthetic feet. These include Flex-Foot® feet such as Ceterus™, LP Ceterus™, Vari-Flex®, LP Vari-Flex®, Talux® and Elation™. Some embodiments of suitable prosthetic feet and associated devices are disclosed in U.S. Pat. No. 5,181,932, issued Jan. 26, 1993, U.S. Pat. No. 5,181,933, issued Jan. 26, 1993, U.S. Pat. No. 5,728,177, issued Mar. 17, 1998, U.S. Pat. No. 5,766,265, issued Jun. 16, 1998, U.S. Pat. No. 5,800,569, issued Sep. 1, 1998, U.S. Pat. No. 6,511,512, issued Jan. 28, 2003, U.S. Patent Application Publication No. 2003/0093158, published May 15, 2003, U.S. patent application Ser. No. 10/642,125, filed Aug. 15, 2003, U.S. patent application Ser. No. 10/674,736, filed Sep. 30, 2003, and U.S. patent application Ser. No. 10/742,455, filed Dec. 18, 2003, the entirety of each one of which is hereby incorporated by reference herein.

The prosthetic knee 10 generally comprises a variable-torque magnetorheological (MR) actuator assembly or braking system 12 and a frame and electronics assembly or system 14 that also serves as a mount for the knee actuator 12 and facilitates in monitoring and controlling the operation of the knee actuator 12. The prosthetic knee system 10 desirably provides resistive forces to substantially simulate the position and motion of a natural knee joint during ambulation and/or other locomotory activities performed by the amputee.

Advantageously, the prosthetic knee 10 of embodiments of the invention permits the amputee to move and/or adapt comfortably and safely in a wide variety of circumstances. For example, during walking, running, sitting down, or when encountering subtle or drastic changes in the terrain, topography and environment or ambient conditions, such as, when the user lifts a suitcase or walks down a slope or encounters stairs, among others.

The prosthetic knee 10 provides stance control to limit buckling when weight is applied to the limb. In addition, the prosthetic knee 10 provides aerial swing control so that the knee reaches full extension just prior to or at heel-strike in a smooth and natural manner. Moreover, the prosthetic knee 10, by adjusting and/or fine tuning the range and/or magnitudes of the resistive torque level, can be adapted for use with a wide variety of patients having different body weights, heights and activity levels.

The prosthetic knee assembly 10 of embodiments of the invention has particular efficacy when used in conjunction with a trans-femoral (above-knee, A/N) amputee. In modified embodiments, the prosthetic knee joint 10 may be efficaciously adapted for use with a knee-disarticulation (K/D) amputee wherein the amputation is through the knee joint, as needed or desired.

FIGS. 1B-1E show a system overview of the prosthetic knee assembly 10 generally comprising the magnetorheological actuator assembly or system 12 and the frame and electronics assembly or system 14. The frame and electronics assembly 14 also provides power and communicates with the actuator assembly 12 via electrical signals.

Figure 1F:
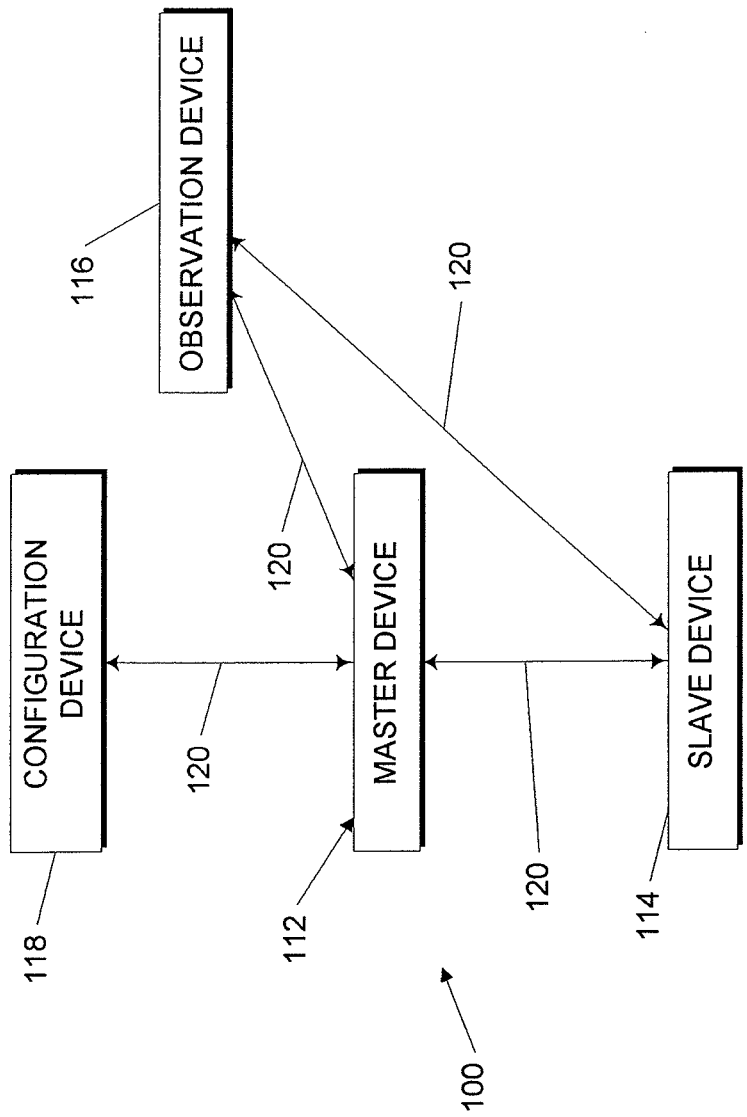
FIG. 1F is a block diagram that illustrates one embodiment of a system including a number of mechatronic devices.

Users of prosthetic or orthotic devices often may need more than one device. For example, a trans-femoral amputee may require a combination of a mechatronic knee and a mechatronic ankle or foot. Typically, more natural movement may be achieved when these devices are coordinated. Where two or more of these devices are electronically controlled devices, improved coordination, e.g., from a more natural motion, can be achieved by electronic interface and coordination between the devices. FIG. 1F is a block diagram that illustrates one embodiment of a system 100 which includes multiple mechatronic devices. In one embodiment, a particular mechatronic device includes one or more sensors, a controller, and one or more actuators. However, it is to be recognized that in other embodiments a particular mechatronic device may include, for example, only sensors, sensors and a controller, one or more actuators, actuators and a controller, or only a controller. In one embodiment, the system may include a master device 112. In one embodiment, the master device 112 directs control of the entire system 100. In one embodiment, the master device 112 is a mechatronic device that has a control system which incorporates a state machine. The master device 112 may fully or partially control a slave device 114. Information on state changes or direct actuation commands may be sent to components of the system 100, such as the slave device 114. Embodiments of each of the devices in the system 100 may include prosthetic knees, prosthetic ankles, or other electronically controlled prosthetic or orthotic devices. For example, an orthotic device such as a brace may include a sensor for measuring knee motion.

In one embodiment, the slave device 114 may only include a portion of the software or hardware needed to control the slave device 114. The slave device 114 may thus be wholly or partially dependent on receiving state information and commands from the master device 112. In one embodiment, the slave device 114 may receive sensor data from the master device 112, or another slave device 114. The slave device 114 may also send sensor data to other devices 112, 114, 116, or 118. In one such embodiment, the slave device 114 includes one or more sensors but does not include an actuator.

The system 100 may include an observation device 116 that is configured to monitor or control one or more of the other devices in the system 100. In one embodiment, the observation device includes a wristwatch, or arm mounted device, that provides status or other information regarding the operation of devices in the system 100. In one embodiment, the status information is updated in real-time. In another embodiment, the observation device 116 may have controls configured to affect the operation of the system 100. In one such embodiment, the observation device 116 includes only a controller that is configured to receive sensor data and/or send control data to other mechatronic devices in the system 100. For example, in one embodiment, the master device 112 may be a prosthetic knee and the observation device 116 may be used for activation or to provide hints as to different use modes, e.g., walking, bicycling, etc.

The system 100 may also include a configuration device 118 that is adapted to control one or more of the other devices in the system. In one embodiment, the configuration device 118 is in direct communication with the master device 112. The master device 112 coordinates communication of configuration data with other devices, e.g., the slave device 114 or the observation device 116. In other embodiments, the configuration device 118 may be in direct communication with all or any subset of the devices 112, 114, 116.

Each of the devices 112, 114, 116, and 118 of the system 110 may communicate using a bionic data bus (BDB) 120. The BDB 120 may comprise any data communications physical layer, including those known in the art. For example, the BDB 120 may include one or more of the following communications layers: a remote modem, Ethernet (IEEE 802.3), Token Ring (IEEE 802.5), Fiber Distributed Datalink Interface (FDDI) Asynchronous Transfer Mode (ATM), Wireless Ethernet (IEEE 802.11), Bluetooth (IEEE 802.15.1), or infrared interfaces including IRDA. The BDB may also include a peripheral interface bus including Universal Serial Bus (USB), IEEE 1394, Peripheral Component Interconnect (PCI), or other peripheral buses such as those known in the art. In addition, the BDB 120 may include networks such as an Intranet, a Local Area Networks (LAN), a Wide Area Network (WAN), or the Internet. The BDB 120 may include additional protocols such as interne protocol (IP) or transmission control protocol (TCP).

It will be recognized that while, in one embodiment, a mechatronic device may operate as one of the devices 112, 114, 116, and 118, in other embodiments of the system 100, a particular mechatronic device may be configured to operate in different modes or roles as one or more of the devices 112, 114, 116, and 118. In one embodiment, the particular mechatronic device may be configured to automatically act as a particular type of device based on data exchange with other devices in the system 100. For example, one embodiment of the system 100 may include a prosthetic knee, a prosthetic ankle, and a wrist-attached monitor. Embodiments of prosthetic knees may include those illustrated in U.S. Pat. No. 6,610,101, filed Mar. 29, 2001, and issued on Aug. 26, 2003; U.S. patent application Ser. No. 11/123,870, filed May 6, 2005; and U.S. Patent Publication No. 2005-0283257, filed on Mar. 9, 2005; each of which is incorporated by reference in its entirety. Embodiments of prosthetic ankles may include those illustrated in U.S. Patent Publication No. US 2005-0197717, filed Feb. 11, 2005, and which is incorporated by reference in its entirety.

After exchanging identifying data over the BDB 120, the knee may configure itself to operate as the master device 112, the ankle may configure itself to operate as a slave device 114, and the wrist monitor to configure itself as an observation device 116. In another embodiment of the system 100 that includes only the ankle and the wrist monitor, the ankle may configure itself as the master device 112 and the monitor as the observation device 116.

In one embodiment, devices may include a configuration database. The database may contain data relating configurations of the system 100 with the role of the device. For example, the ankle device may include data indicating that the ankle should configure itself as the slave device 114 when the system 100 includes a knee prosthetic, but should configure itself as the master device 112 in other configurations.

It will be further recognized that in some embodiments, the system 100 may include one or more of each of the slave device 114, observation device 116, and configuration device 118. Further, in some embodiments, multiple master devices may be configured such that the devices each control groups of prosthetics, e.g., one master device 112 for a group of arm based mechatronic devices and a second master device 112 for a group of leg based mechatronic devices. In such an embodiment, the observation device 116 may display information related to some of the master and slave devices 112 and 114. In another embodiment, each observation device 116 may display information related only to a single master or slave device 112 or 114.

The master devices 112 may communicate over the BDB 120 to share data or otherwise coordinate operation of the system 100. In one such embodiment, each of, e.g., arm and leg mechatronic devices may operate as the master device 112 with respect to a group of devices. For instance, the knee may operate as the master device 112 with respect to an ankle prosthesis and a shoulder mechatronic device may act as a master device 112 to an elbow slave device 114. Continuing with this exemplary embodiment, with respect to knee master device 112, the ankle may operate as a slave device 114.

It will be recognized that the devices 112, 114, 116, 118 as described herein refer to roles or functional descriptions of one mode of operation of a mechatronic device. In some embodiments, a mechatronic device may be a hybrid device, e.g., one that acts as a slave device 112 under the influence or direction by another master device 112, but which also maintains a distinct state machine. Further, other embodiments may include mechatronic devices that operate as combinations of any of the devices described herein.

Figure 2:
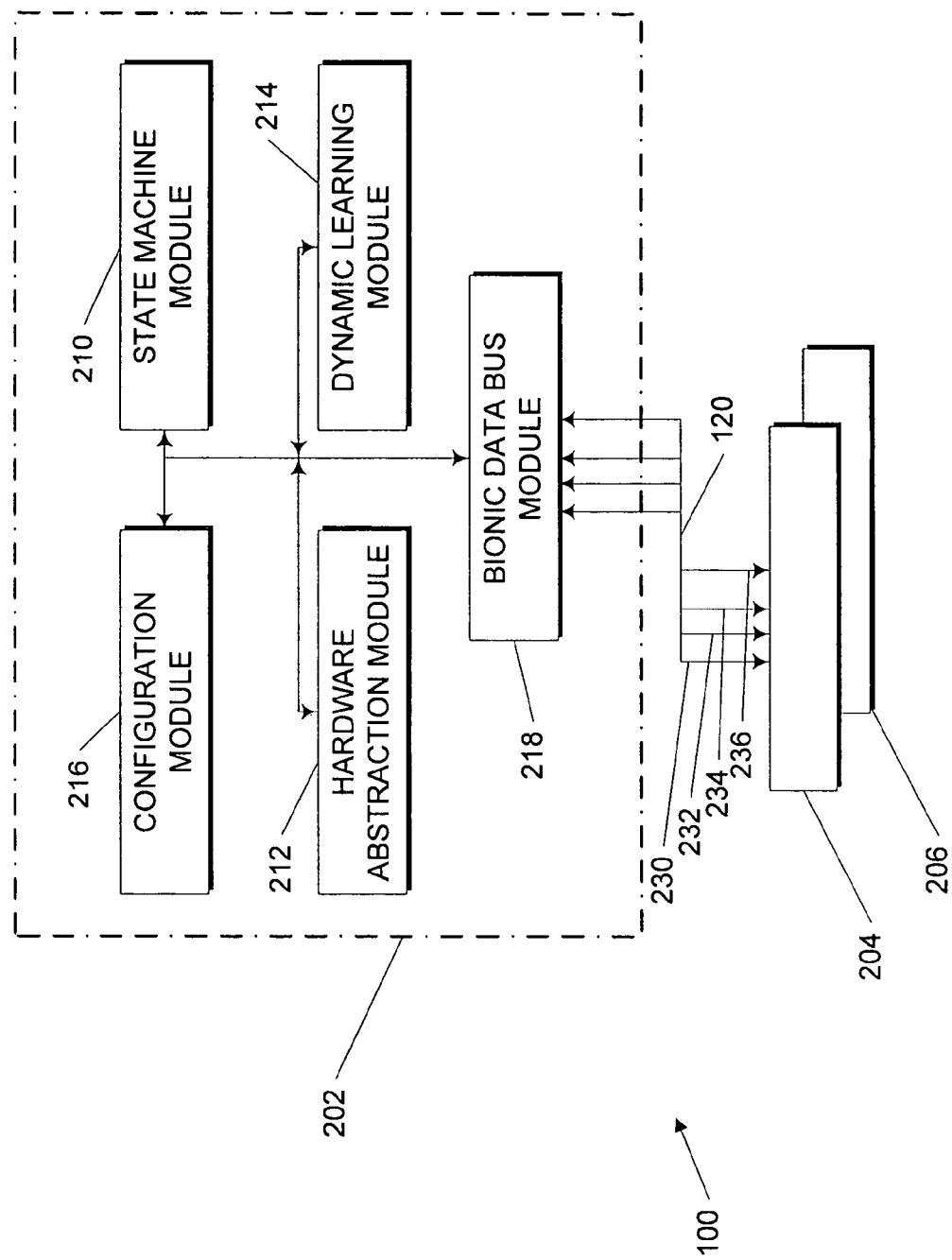
FIG. 2 is a block diagram illustrating in more detail one embodiment of a mechatronic device in communication with additional devices in one embodiment of the system of FIG. 1F.

FIG. 2 is a block diagram illustrating in more detail one embodiment of a mechatronic device 202 in communication with additional devices 204 and 206 in one embodiment of the system 100 via the BDB 120. The device 202 may include a processor and memory configured to execute software for controlling the operation of the device.

In one embodiment, the software includes a state machine module 210, a hardware abstraction module 212, a dynamic learning module 214, a configuration module 216, and a BDB module 218. It will be recognized that each of the modules 210, 212, 214, 216, and 218 may include various sub-routines, procedures, definitional statements and macros. Each of the modules may be separately compiled and linked into a single executable program. The description of each of the modules is used for convenience to describe the functionality of one embodiment of a system. Thus, the processes that are performed by each of the modules may be redistributed to one of the other modules, combined together in a single module, or made available in, for example, a shareable dynamic link library. In some embodiments, the modules may be executed concurrently or in parallel as distinct threads or processes. The modules may be produced using any suitable computer language or environment, including general-purpose languages such as C, C++, Java, or FORTRAN.

Each of the modules 210, 212, 214, 216, and 218 may communicate via any suitable method such as are known in the art. In one embodiment, the modules may communicate using shared data structures such as are described in U.S. Patent Publication No. 2005-0283257, filed on Mar. 9, 2005, which was previously incorporated herein. In one embodiment, the shared data structure may include portions that are available for access through the bionic data bus module 218 to other devices 204 and 206 in the system 100. In such an embodiment, portions of the data in the shared structure may be communicated on the BDB 120.

In one embodiment, the observation device 116 may be a personal or server computer system configured to perform diagnostic functions of other devices in the system 100. In one embodiment, the observation device 116 may be configured to receive and update the contents of shared data structures, such as described above, through the bionic data bus module 218.

The state machine module 210 typically includes high level, application or device specific instructions. The state machine module 210 may be generally described as having the intelligence of the device. The state machine module 210 of a particular embodiment of a mechatronic device may be configured to operate as the master device 112, the slave device 114, the observation device 116, or the configuration device 118 in various embodiments of the system 100. An embodiment of the state machine module 210 may be configured so as to be loaded into different mechatronic devices, e.g., different knee hardware, without modification by using the hardware abstraction module 212 to interface with specific hardware on a particular mechatronic device. One exemplary embodiment of a state machine module 210 is described in U.S. Pat. No. 6,610,101, filed Mar. 29, 2001, and issued on Aug. 26, 2003, incorporated above.

In one embodiment, portions of the state machine module 210 may be replaced or augmented to provide customized, e.g., activity based, control of the mechatronic system 100. For example, software for a specific activity, e.g., bicycling or jogging, may be installed into the state machine module 210 to improve or customize the functionality of the mechatronic device, e.g., a prosthetic knee, for the specific activity. In one embodiment, the customized control software is installed via download. In one embodiment, the downloaded data may be received from the configuration device 118. In another embodiment, the master device 112 may include a network interface over which the customized control software may be received from any other networked computing device. The network interface may comprise a wireless network, e.g., a mobile telephone network, or any other suitable computer network, such as those discussed above in connection with the BDB 120.

The hardware abstraction module 212 typically includes low level, hardware specific code that provides a standardized interface to the hardware by other software modules. The hardware abstraction module 212 may abstract hardware such as sensors and actuators. The hardware abstraction module 212 thus allows other software, such as the state machine module 210 to be reused with different sensors so long as the sensors each provide data that the hardware abstraction module 212 can represent in a standardized form. For example, a particular sensor may provide data via setting the value of a hardware register. Another sensor for producing equivalent data may signal the processor via an interrupt when the data is updated. The hardware abstraction layer 212 can be configured to read either sensor and provide the data using a uniform interface so that other software layers do not need to be modified if the particular sensor changes. This may be particularly desirable in the system 100 having multiple mechatronic devices 202, 204, 206. For example, an ankle mechatronic device 202 may be configured to receive a sensor value, e.g., a knee angle, from different types and models of prosthetic knees 204. Continuing this example, the hardware abstraction layer 212 of the ankle device 202 may provide, in one embodiment, a knee angle that is updated every 5 milliseconds regardless of whether the sensor is configured to be polled by the processor to receive updates or whether the sensor signals the processor via, e.g., an interrupt channel. The hardware abstraction layer 212 may also be configured to provide the knee angle value that is upsampled or downsampled to a consistent, accurate value regardless of the sensor resolution. For example, the knee angle value may be represented with a value having a resolution of 8 bits, 10 bits or higher. Moreover, the interface to the data may be the same regardless of whether the data is coming from the same mechatronic device 202 or other mechatronic devices 204, 206.

It is to be recognized that some embodiments include mechatronic devices in which the hardware abstraction layer 212 is configured to communicate with a patient's nervous or muscular system. For example, the actuator may include a muscle. In one embodiment, a sensor includes a nerve of the patient's body.

The dynamic learning module 214 may include a dynamic learning matrix that updates runtime parameters such as may be used by the state machine module 212. In one embodiment, the learning module 214 may adapt runtime parameters to the current pace of movement, particular activity, terrain, etc. One exemplary embodiment of a learning module 214 is described in U.S. Pat. No. 6,610,101, filed Mar. 29, 2001, and issued on Aug. 26, 2003, incorporated above.

The configuration module 216 may be configured to store and maintain control parameters. The parameters may be subsequently automatically adjusted by the learning module 214 or through the configuration device 118. In one embodiment, the data maintained by the configuration module 216 is substantially static. The configuration module 216 may be configured to communicate with the BDB 120 to the configuration device 118 to send and receive parameter data. The configuration module 216 may provide a standard interface over the BDB 120 to the configuration device 118. In one embodiment, the configuration module 216, e.g., of the slave device 114 is configured to receive parameters through other devices such as the master device 112. Thus, the components of the system 100 may be configured together through the configuration device 118 in communication with the master device 112, which further communicates parameters to other devices such as devices 204 and 206 in the system 100.

In one embodiment, the abstraction module 212 controls one or more actuators in a mechatronic system 100. In one embodiment, this comprises applying damping through an actuator in, e.g., a prosthetic knee. In one embodiment, at least a portion of the abstraction module 212 executes at a frequency that is different from the execution rate of the state machine or learning modules 210 and 214. For example, in one embodiment the low level abstraction module 212 executes with a period of 1 millisecond (ms) while the higher level code of the state machine executes with a period of 5 ms.

The bionic data bus (BDB) module 218 is configured to provide data communications between devices in the system 100 over the BDB 120. One embodiment of the BDB module 218 includes a software interface that abstracts or standardizes an interface to the other modules 210, 212, 214, and 216 for communicating over the BDB 120 regardless of the particular embodiment of the BDB 120, e.g., regardless of whether the BDB includes a network or a peripheral bus such as USB.

The BDB module 218 may provide a layered interface to the BDB 120. In one embodiment, the layers may correspond to one or more physical channels provided by the BDB 120. In other embodiments, the layers may correspond to logical channels over the BDB 120. In one embodiment, the channels provided by the BDB module 218 includes a state channel 230, a parameter channel 232, a sensor channel 234, and an actuation channel 236.

The state channel 230 may be configured to communicate high frequency, low volume state machine data between mechatronic devices. In one embodiment, this data may include data related to the gait cycle of a prosthetic knee. The data may include state data or state change data. For example, in a prosthetic knee, the state change may indicate a change in a gait cycle.

The parameter channel 232 may be configured to communicate data at intermediate frequencies and volumes to communicate parameter settings between devices, e.g., between the configuration device 118 and the master device 112. The parameter channel 232 may data may include configuration parameters such as are described in U.S. Patent Publication No. 2005-0283257, filed on Mar. 9, 2005, which was previously incorporated herein.

The sensor channel 234 may be configured to communicate high frequency, low volume sensor data. Sensor data from one device in the system 100 may thus be shared for use by other devices. This allows for placement of sensors in locations that are not physically located in or adjacent to a particular mechatronic device but which are physically located within or adjacent to another device in the system 100. Moreover, certain sensors may thus be shared to reduce overall cost of the system 100. Sensors may include force sensors, battery voltage sensors, or any other sensors as may be incorporated or attached to any mechatronic device.

Another channel may include the actuation channel 236. The actuation channel 236 communicates low volume, high frequency data that includes actuator control signals. In one embodiment, the master device 112 may send actuator control signals over the actuation channel 236 to control an actuator on the slave device 114. The data may include data such as position, force, direction, and velocity.

In addition to communicating with other mechatronic devices, other electronic devices, e.g., a remote server computer (not shown), may communicate with the mechatronic device via the BDB 120. In one embodiment, the remote server may carry out maintenance activities such as diagnosing faults in the mechatronic device. The device 202 may communicate sensor data, state change data, or other data generated on the device 202, or devices 204, 206 attached to the device 202 via the BDB 120.

In one embodiment, a common naming convention is used to identify the data communicated on the channels. In one embodiment, the data is formatted as structured data using the naming convention, such as in extendible markup language (XML). In one embodiment, the naming convention is based on using terminology analogous to anatomical equivalents. For example, in one embodiment, the naming convention includes terminology from the human muscular system for actuator signals and from the human nervous system for sensor signals.

Figure 3:
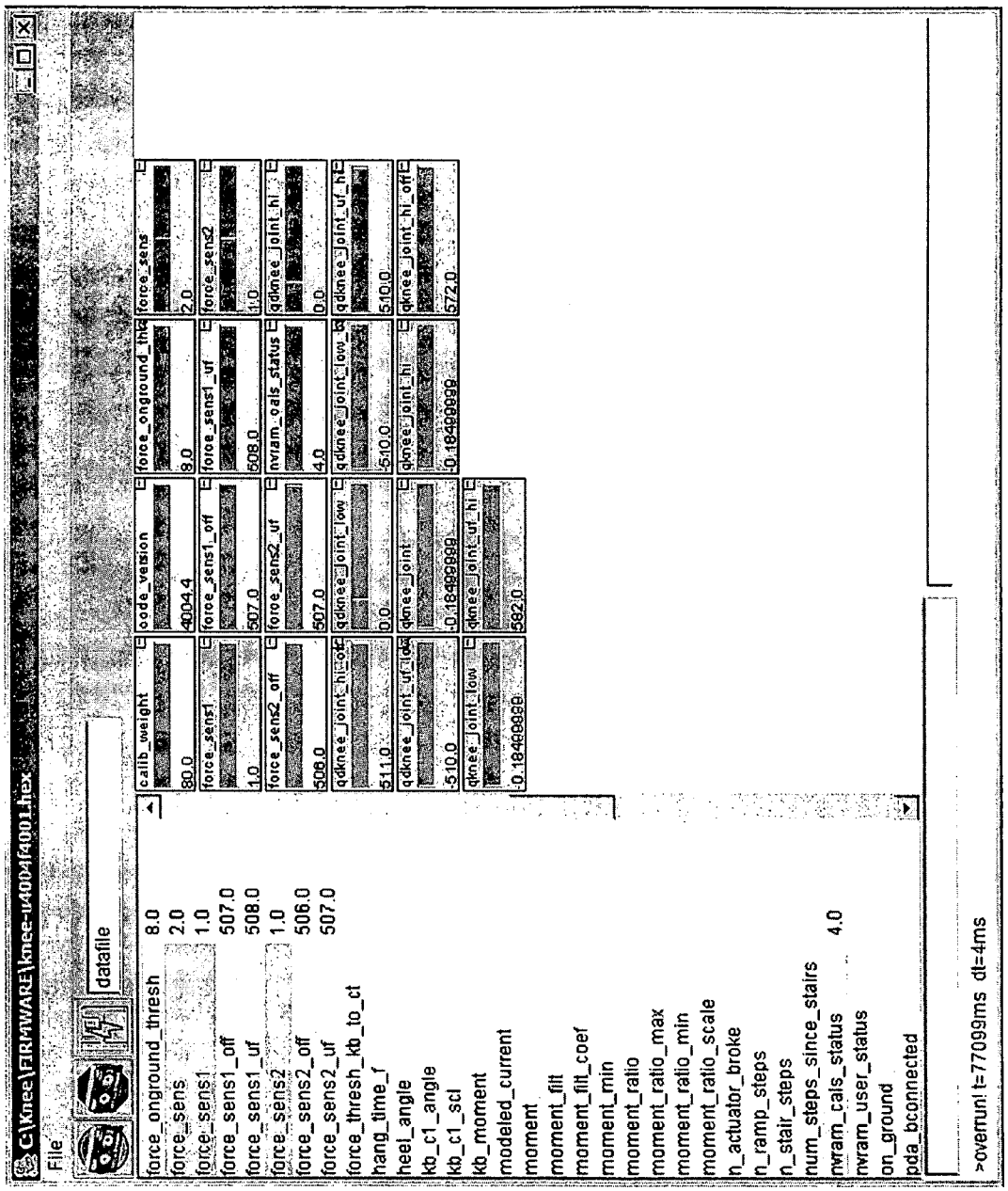
FIG. 3 illustrates a user interface of one embodiment of an instrumentation program for use with a mechatronic device.

In one embodiment, the remote computer includes instrumentation software for maintenance or development of the mechatronic device 202. FIG. 3 illustrates a user interface of one embodiment of the instrumentation program for use with a prosthetic knee. The left column displays the names of memory locations, registers, or other data that may be monitored on the mechatronic device 202. In the depicted embodiment, selecting the name of a monitored item causes the value to be displayed. In one embodiment, the displayed value is continuously and automatically updated when new data is received from the device 202. In one embodiment, the values of the monitored items may be recorded to a file for later analysis. This analysis may include graphical plotting of the data. In one embodiment, the instrumentation program may also send commands to the device 202, such as to erase data, reset the device 202, and update the software or firmware on the device 202. In one embodiment, the values of these items may be modified by a user of the instrumentation program. In one embodiment, the instrumentation program may be configured to restrict the values of the updated items to be set within a predetermined range.

FIG. 4A is a schematic block diagram of an exemplary embodiment of the system 100 that includes a prosthetic knee 402 and a prosthetic ankle 404. When the system 100 includes an electronically controlled ankle 404 and an electronically controlled knee 402 there is a risk of instability if the two "intelligent" components do not share information or otherwise work in a synchronized manner. The knee 402 may include 3 main sensors, an angle sensor, posterior force sensor (PF) and anterior force sensor (AF). From the signals of PF and AF sensors, the knee 402 can calculate the moment in a pylon. The knee 402 can represent the moment as information as to how much the toe is being loaded and how much the heel is being loaded. From the calculation on the values from PF and AF sensors, the knee 402 is also able to tell if the foot is placed on the ground and with how much force. The force signals together with the angle sensor are evaluated by an algorithm in the state machine module to define the state of the knee 402 in a high level loop cycling, in one embodiment, every 5 ms. If the signals are incorrect or misinterpreted, the knee 402 cannot change states or function correctly.

Since the values from the force sensors (bending moment in the knee frame) are translated into toe- and heel load values, the alignment of the foot and especially the angle of the ankle 404 should be determined. During setup, certain ranges and threshold values may be set for the knee 402. If the alignment is changed considerably after the initial setup, the knee 402 can misinterpret the information from the force sensors. The functionality of an electronically adjusted ankle 404 typically causes just such a change in alignment.

If the ankle 404 can send information on the angle value to the knee with a sufficiently high frequency, the knee can compensate for the "error" in force signals from the sensors and the whole system 100 can operate in a more stable way as compared to a non-synchronized system.

The electronic ankle 404 may also be designed to also fit below-the-knee amputees. In such a mode of use, the ankle 404 does not need the extra information from a "colleague" component. The extra information that the knee 402 is able to communicate may however simplify the design of the ankle for use by above-the-knee amputees.

In addition, the use of data by the knee 402 from the ankle 404 can provide additional functionality to the system 100. For example, the angle value of the ankle 402 can be made accessible to the knee 404 through the parameter channel 232 of the BDB 120. Also if the ankle is offset by some degree (for use with high heels, for example), the knee 402 may use the information to further compensate for the force sensor measurements. The offset value can be communicated over the parameter channel 232.

In one embodiment, the ankle may include a prosthetic or orthotic foot, similar to embodiments disclosed in U.S. patent application Ser. No. 11/346,600, filed on Feb. 2, 2006, titled "SENSING SYSTEMS AND METHODS FOR MONITORING GAIT DYNAMICS," and incorporated by reference in its entirety, that is configured to make and provide toe load and heal load measurements over the BDB 120. In another embodiment, the ankle may include a prosthetic or orthotic foot, similar to embodiments disclosed in U.S. patent application Ser. No. 10/742,455, filed on Dec. 18, 2003, titled "Prosthetic foot with rocker member," and incorporated by reference in its entirety, that is configured to make and provide an angle measurement over the BDB 120.

FIG. 4B is a schematic block diagram of an exemplary embodiment of the system of FIG. 1F that includes a prosthetic knee 402 and a prosthetic foot 406. In one embodiment, the knee 402 and the foot 406 each include a data communications or network interface such as an RS-232 port that are in communication with each other to define the BDB 120. In another embodiment, the BDB 120 may be implemented via RS-485 ports on each of the devices 402 and 406. In one embodiment, the prosthetic foot 406 includes a joint that allows the foot to adjust to different grades of slopes. As a result, the response from the foot 406 will differ from prosthetic feet with a fixed ankle. In one embodiment, the knee 402 is controlled based on force measurements that are translated into bending moments. From the moment values, the knee 402 manages state changes and adjusts the resistance of the knee based on whether the knee 402 is on level ground, on different grades of slopes, or on stairs.

In one embodiment, the knee 402 may detect that the user is walking on a sloped surface based on changes in force and moment. Due to bending of the jointed foot 406, the foot 406 may adjust to a slope so that the knee 402 does not receive force measurements that are consistent with walking on the slope. Thus, the knee 402 may act as if the user is walking on level ground when the user is actually descending a ramp. In one embodiment, the foot 406 may communicate its joint angle to the knee 402 when the angle has changed. In other embodiments, the foot 406 may communicate the angle to the knee at a predetermined rate or when the angle changes by a threshold amount. In one embodiment, the knee 402 may request the data from the foot 406 either at intervals or response to particular events such as state changes. The knee 402 may then use the angle value to correct the moment calculations (e.g., through a proportional calculation as a function of the angle). In one embodiment, the data communicated from the foot 406 to the knee 402 may include state machine data. The state machine data may be used by the control system of the knee 402 to coordinate movement with the foot 406 and to better identify the proper control response based on the additional information from the foot 406, e.g., correcting force sensor readings when the joint of the foot 406 is bent.

Data may be communicated between the foot 406 and the knee 402 using any suitable protocol such as discussed above with reference to the BDB in FIG. 1F. For example, in one embodiment, sensor and control data may be communicated as a string of characters over the RS-232 link. In one embodiment, in each program cycle of the knee 402, the knee reads the serial port, parses the string and filters out the angle value. The angle value is then translated into a correction value for a slope detection routine.

In another embodiment, data may be communicated over the RS-232 layer by a suitable link layer protocol such as the High Level Link Control (HDLC) protocol. In other embodiments, suitable higher level protocols may be used. In one embodiment, the two RS-232 ports may be connected via simple wire interface.

In one embodiment, the knee 402 may operate as the master device 112 that receives sensor data from the foot 406 and use that data to generate control signals that are communicated back to the foot 406. In such an embodiment, the additional sensor data from the foot 406 may be used to provide control that is more robust and enable the knee 402 to be better able to anticipate or otherwise manage state changes. Moreover, the additional sensor data of the knee can be used to extend or improve the control of the foot 406. For example, the load sensors of the knee 402 may be able to detect a rapid toe off signal that can indicate initial steps onto stairs. The control system of the foot 406 may be configured to use this data to anticipate and better detect state changes such as stair ascent or descent.

In one embodiment, the foot 406 and the knee 402 may also be configured to share a power source. In such an embodiment, the master device 112, e.g., the knee, may coordinate power management for both devices. In one embodiment, the foot 406 and knee 402 may be designed specifically to operate together. However, in other embodiments, any knee 402 and foot 406 that include compatible mechanical and communication interfaces may form the system 100.

FIG. 4C is a schematic block diagram of another exemplary embodiment of the system of FIG. 1F that includes a prosthetic knee 402, a prosthetic foot 406, and a master device 408 operating as a master device 112. The master device 408 may include any electronic device configured to receive sensor data from each of the knee 402 and the foot 406 and provide control signals to the knee 402 and the foot 406 based on that sensor data.

FIG. 4D is a schematic block diagram of another exemplary embodiment of the system of FIG. 1F that includes a prosthetic knee 402 and a prosthetic foot 406 in which the prosthetic foot 406 operates as the master device 112. In such an embodiment, the controller of the foot 406 may include one or more state machines for controlling both devices.

FIG. 5 is a block diagram that depicts one embodiment of a system 500 for communicating with a pair of mechatronic devices 202 and 204. In the depicted embodiment, the system 500 includes a single network computing device 340 in communication with the mechatronic devices 202 and 204 via a data communications network 350. Other embodiments include only a single mechatronic device 202, or more than two mechatronic devices. In one embodiment, the system 500 includes additional network computing devices 341 that are also in communication with the network computing device 340 via a network 352. In one embodiment, the mechatronic devices 202 and 204 are configured to communicate with the network computing device 340 to send and receive configuration and calibration data. In one embodiment, the mechatronic devices 202 and 204 are configured to communicate with the network computing device 340 to receive executable instructions to augment or replace portions, or all, of one or more of the state machine module 210, the hardware abstraction module 212, the dynamic learning module 214, a configuration module 216, the BDB module 218, or any other suitable software module of the mechatronic device 202.

In one embodiment, the network computing device 340 includes a network interface 342 in communication with a processor 344 and a memory 346. The network computing device 340 may include a server computer, a personal computer, or a mobile computer such as a laptop computer. In one embodiment, the network computing device 340 includes a personal digital assistant. In another embodiment, the network computing device 340 includes a mobile telephone.

The network interface 342 provides network connectivity to one or more computing devices, including the mechatronic devices 202 and 204, via the networks 350 and 352. In one embodiment, the network interface 342 to the networks 350 and 352 includes one or more of, for example, a remote modem, Ethernet (IEEE 802.3), Token Ring (IEEE 802.5), Fiber Distributed Datalink Interface (FDDI) Asynchronous Transfer Mode (ATM), Wireless Ethernet (IEEE 802.11), Bluetooth (IEEE 802.15.1), or infrared interfaces including IRDA. The network 350 may include networks such as the Internet, an intranet, Local Area Networks (LAN) or Wide Area Networks (WAN). As used herein, the networks 350 and 352 may include network variations such as the public Internet, a private network within the Internet, a secure network within the Internet, a private network, a public network, a value-added network, an intranet, and the like. In one embodiment, the network 350 includes the network 352.

The processor 344 may be any suitable general purpose single- or multi-chip microprocessor such as an ARM, Pentium®, Pentium II®, Pentium III®, Pentium IV®, Pentium® Pro, an 8051, a MIPS®, a Power PC®, an ALPHA®, or any other suitable processor. In addition, the processor 344 may comprise any suitable special purpose microprocessor such as a digital signal processor or a programmable gate array.

The memory 346 may include volatile components, such as, for example, DRAM or SRAM. The memory 346 may also include non-volatile components, such as, for example, memory or disk based storage. In one embodiment, the network computing device 340 includes a server and the memory 346 includes disk base storage. In one embodiment, the disk based storage includes a file server.

In one embodiment, the mechatronic device 202 includes a storage card interface 366 to a removably connected memory. The storage card interface 366 may include an interface to a removable storage card that includes semiconductor storage (chips), for example, Random Access Memory (RAM) or various forms of Read Only Memory (ROM), that are removablely connected to the processor 344. Removably connected memory may include memory on any standardized or proprietary device such as a memory card, a secure digital memory card, a memory stick, or any other suitable removable memory device. In one embodiment, the storage card interface 366 is configured to interface the processor solid state persistent memory such as FLASH memory or magnetoresistance RAM (MRAM). In one embodiment, the memory includes a disk drive, e.g., a magnetic, optical, or magneto-optical drive.

In one embodiment, each of the mechatronic devices 202 and 204, includes a processor 360 connected to a memory 362 and a network interface 364. The processor 360 may include any suitable processor including those discussed above with respect to the processor 344. The memory 362 may include any suitable memory such as discussed above with respect to the memory 346. The network interface 364 places the processor 360 in communication with the network 350. The network interface 364 may include any suitable network interface, including those discussed above with respect to the network interface 342.

Figure 6:
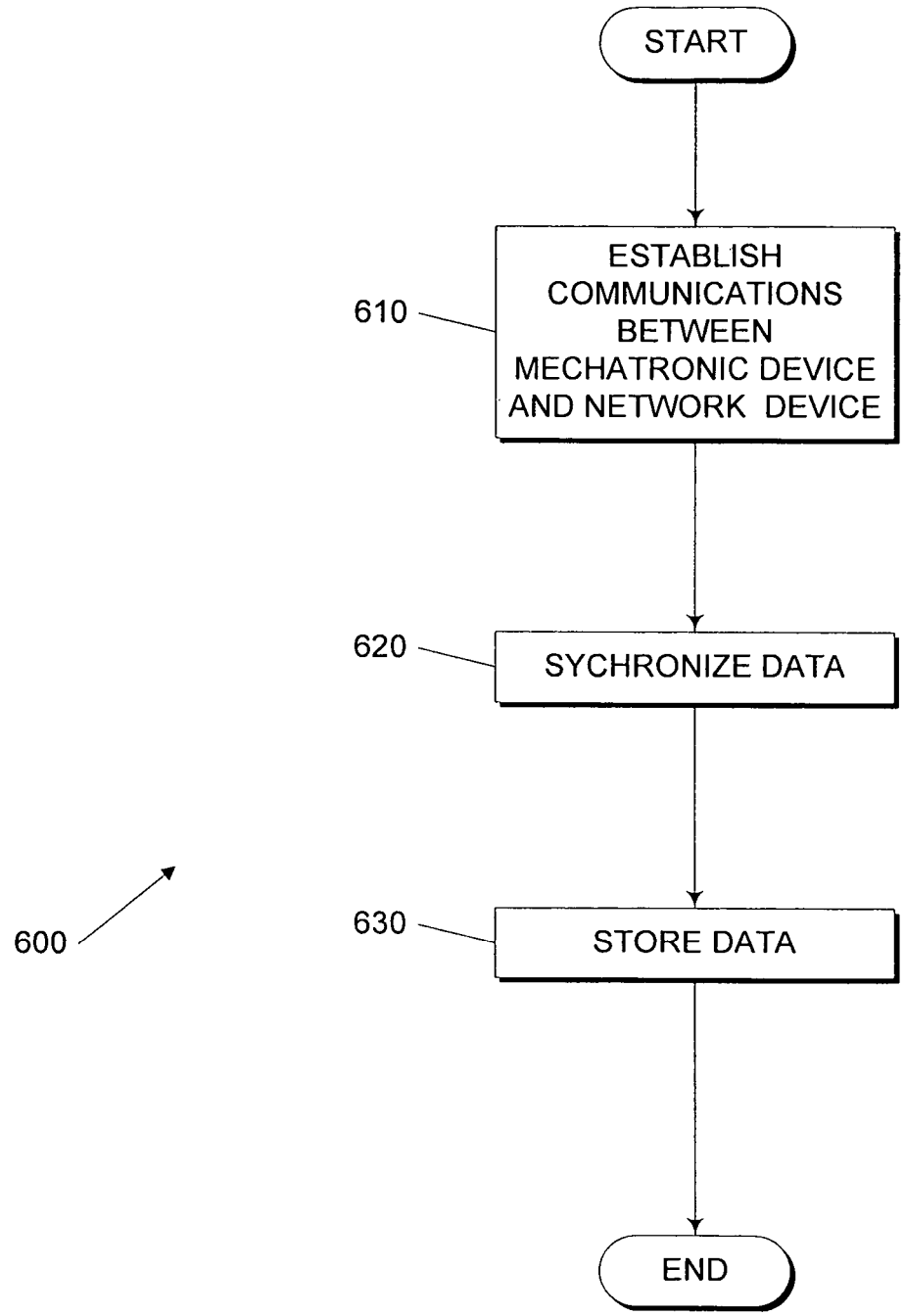
FIG. 6 is a flowchart illustrating one embodiment of a method of synchronizing configuration or calibration data of the mechatronic device with the network computing device.

FIG. 6 is a flowchart illustrating one embodiment of a method 600 of synchronizing configuration or calibration data of the mechatronic device with the network computing device 340 of FIG. 5. Configuration data may include data that is entered by a prosthetist, determined based on predetermined parameters, such as the height of a user of the mechatronic device, selected based on experience or preferences of the user of the mechatronic device 202, or selected by a designer or manufacturer of the mechatronic device, that affects the control system of the mechatronic device 202. Calibration data may include data that is determined by the control system of the mechatronic during operation of the mechatronic device 202. Such data may also be generally referred to as control data. The method 600 begins at a block 610 in which the mechatronic device 202 establishes communications with the network computing device 340. Entry or examination of such data could be made through a screen display such as the one shown in FIG. 3.

Next at a block 620, the mechatronic device 202 synchronizes one or more settings with the network computing device 340 of FIG. 5. In one embodiment, the mechatronic device 202 receives configuration or calibration information related to a user of the particular mechatronic device 202. In another embodiment, the mechatronic device 202 sends configuration or calibration data to the network computing device 340. In one embodiment, the synchronized configuration and calibration data includes any of the data, discussed above, that is sent over the BDB 120. In addition, the synchronized data may include any other configuration or calibration data used by the mechatronic device 120.

In one embodiment, synchronizing the data includes determining the differences between data on the mechatronic device 202 and data associated with the particular mechatronic device 202 on the network computing device 340, and sending that data from one device to the other. In one embodiment, the network computing device 340 stores the data associated with the mechatronic device 202 in a database in association with data identifying the particular mechatronic device, e.g., a serial number. In one embodiment, when the particular mechatronic device 202 is synchronized again, the network computing device 340 determines the differences in the data based on the data in the database. In one embodiment, after determining which control data is different, the mechatronic device 202 sends control data to the network computing device 340 that overwrites control data associated with the mechatronic device 202. In another embodiment, the network computing device 340 sends control data to the mechatronic device 202 that overwrites such data on the mechatronic device. In one embodiment, some data is sent both ways for overwriting. Whether the control data is sent to or from the mechatronic device 202 may be based on one or more methods. For example, in one embodiment, time stamps are associated with the data so that the newest data associated with a particular item of control data is saved on both the mechatronic device 202 and the network computing device 340. In other embodiments, predetermined rules regarding particular items of control data determine how the data is synchronized. In one embodiment, a selection by the user of the device, or a selection by a prosthetist determines in which data particular items of control data are synchronized. In one embodiment, a new mechatronic device 202 receives initial control data from a database associated with the network computing device 340 that stores initial data or overwrites any existing data on the mechatronic device 202.

In one embodiment, the network computing device 340 acts as a conduit to send and receive the configuration or calibration data to another network computing device 341 that stores the data. In one embodiment, the network computing device 340 is a PDA or mobile telephone that communicates with the mechatronic device 202 via a short range network and relays that data to the network computing device 341. In one such embodiment, the network computing device 341 includes a server computer. Thus, the mechatronic device 202 may synchronize configuration and calibration data with one or both of the network computing devices 340 and 341.

Next at a block 630, the mechatronic device 202 stores any received data. Also, or alternatively, the network computing devices 340 and 341 store any received data. In one embodiment, one or more of the devices 202, 340, or 341 also store data related to the synchronization, e.g., a timestamp or data identifying the devices or data involved in the synchronization. In one embodiment, the network computing device 340 or 341 stores the data in a database in association with the mechatronic device. Returning to FIG. 6, the method 600 proceeds to an end state.

Figure 7:
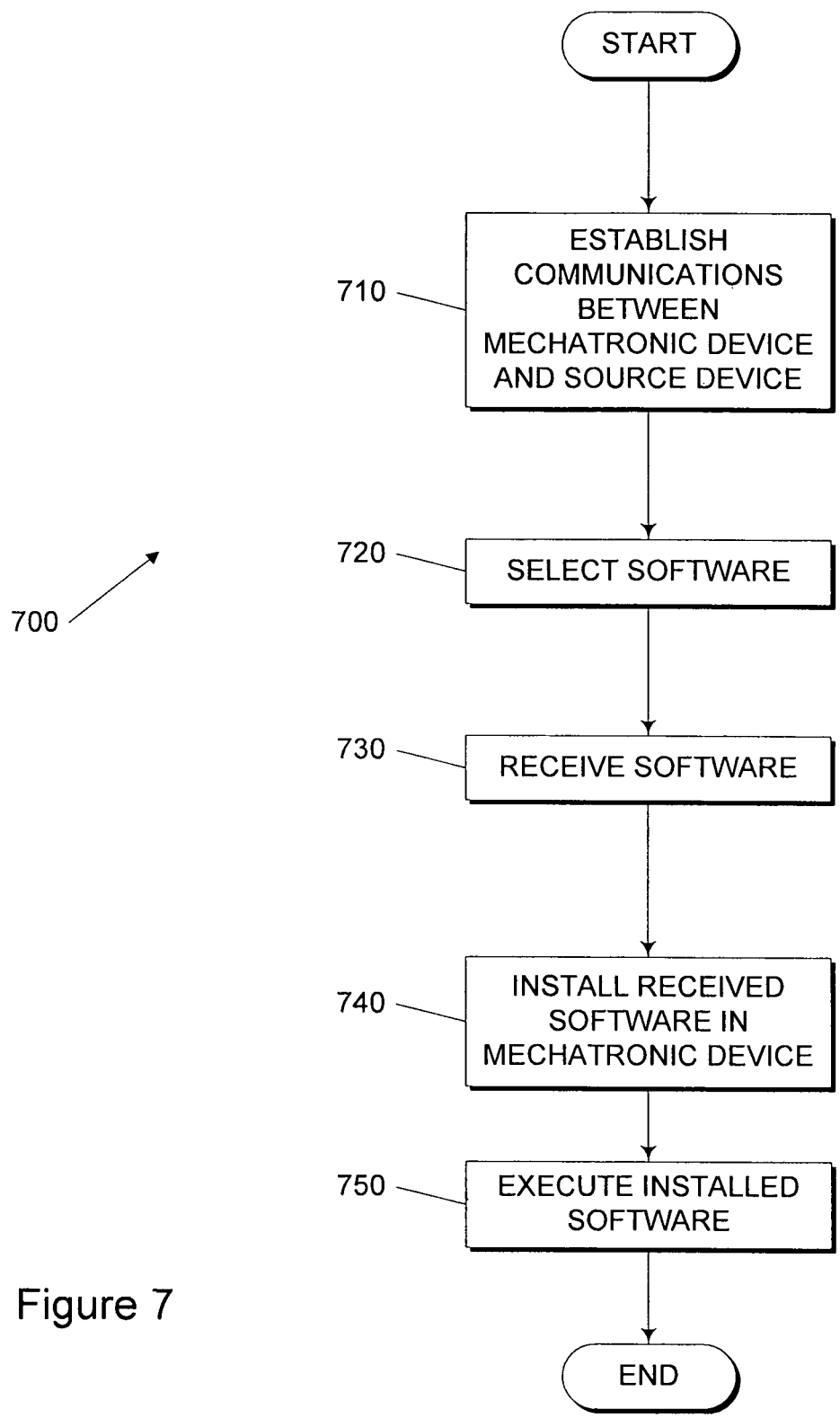
FIG. 7 is a flowchart illustrating one embodiment of a method of replacing or augmenting software on the mechatronic device.

FIG. 7 is a flowchart illustrating one embodiment of a method 700 of installing, replacing, augmenting, or deinstalling software on the mechatronic device. The method 700 begins at a block 710 in which the mechatronic device 202 establishes communication with a source device containing software configured to execute on the mechatronic device 202. In one embodiment, the source device includes the network computing device 340. In such an embodiment, the mechatronic device 202 establishes communications with the network computing device 340 via the network 350. In another embodiment, the source device also includes the network computing device 341. In such an embodiment, the mechatronic device establishes communications with the network computing device 341 through the networks 350 and 351 via the network computing device 340. In one embodiment, the source device includes another mechatronic device. In another embodiment, the source device includes a storage card in communication with the storage card interface 366. The software could be low level firmware and/or high level software, for example.

Moving to a block 720, the mechatronic device 202 or the user of the device 202 selects software to be installed thereon. In one embodiment, the user selects from a list of software adapted to various activities, e.g., hiking, biking, or jogging. In one embodiment, the list is displayed on a user interface associated with the network computing device 340. In one embodiment, the user interface includes a web browser. In one such embodiment, the user interface receives the list from the network computing device 341.

Proceeding to a block 730, the mechatronic device 202 receives the software from the source device. In one embodiment, receiving the software includes transferring then software over the network 350. In another embodiment, receiving the software includes having a storage card installed in the storage card interface 366.

Next at a block 740, the mechatronic device 202 installs the software for execution. Installing the software may include saving the software to a portion of the memory 362, updating pointers or jump tables in the memory 362 to replace or augment previously installed software, or storing a record of the software installation. In one embodiment, the record includes sufficient data to remove the newly installed software. In one embodiment, the mechatronic device 202 saves the received software to its memory 362. In another embodiment, the mechatronic device 202 executes the new software directly from a storage card.

Moving to a block 750, the mechatronic device executes the new software. The new software may replace all or a portion of one or more of the state machine module 210, the hardware abstraction module 212, the dynamic learning module 214, a configuration module 216, the BDB module 218, or any other suitable software module of the mechatronic device 202. The new software may include software updates to fix bugs, improve performance, or provide additional features. In one embodiment, the new software may include instructions for controlling the mechatronic device 202 to perform one or more specific activities such as hiking, biking, swimming, jogging, throwing, jumping, or for movement over a particular type of terrain.

It is to be appreciated that depending on the embodiment, certain acts or events of a method described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

What is claimed is:

1. A mechatronic system attachable to a human body, the system comprising:
   a prosthetic joint;
   at least one sensor configured to gather data regarding a motion parameter of the prosthetic joint;
   an actuator configured to control movement of the prosthetic joint;
   a memory storing a first set of instructions for controlling the actuator based on the sensor data;
   a communication interface configured to communicate data with a data source external to the prosthetic joint, the communicated data comprising a second set of instructions for controlling the actuator based on the sensor data; and
   a processor configured to execute the stored first set of instructions, execution of the first set of instructions causing the processor to determine a first actuator control command based on the sensor data that controls movement of the prosthetic joint according to a first activity, the processor further being configured to receive and execute the second set of instructions, execution of the second set of instructions causing the processor to determine a second actuator control command based on the sensor data that controls movement of the prosthetic joint according to a second activity, the first actuator control command being different than the second actuator control command, and the first activity being different than the second activity, wherein the memory is further configured to store the second set of instructions, wherein the stored second set of instructions replaces the stored first set of instructions in the memory.

2. The mechatronic system of claim 1, wherein the prosthetic joint is a lower limb prosthetic joint.

3. The mechatronic system of claim 1, wherein each of the first activity and the second activity is one of the following: bicycling, jogging, hiking, swimming, throwing, jumping, or movement over a particular terrain.

4. The mechatronic system of claim 1, wherein the communicated data further comprises diagnostic information of the mechatronic system sent to the data source.

5. The mechatronic system of claim 1, wherein the communication interface is configured to transmit data to the data source and receive data from the data source.

6. The mechatronic system of claim 1, wherein the first set of instructions comprises a first state machine module.

7. The mechatronic system of claim 6, wherein the first state machine module comprises at least one of: sub-routines, procedures, definitional statements, and macros.

8. The mechatronic system of claim 1, wherein the first set of instructions comprises code written in a computer language that has been compiled and is capable of being executed by the processor.

9. The mechatronic system of claim 1, wherein the data source comprises a computing device.

10. The mechatronic system of claim 9, wherein the computing device comprises a mobile telephone, a personal digital assistant or a mobile computer.

11. The mechatronic system of claim 1, wherein the communication interface is at least one of a wired network interface or a wireless network interface.

12. The mechatronic system of claim 11, wherein the communication interface is configured to communicate data using an internet protocol.

13. The mechatronic system of claim 1, wherein the data source stores the second set of instructions for controlling the actuator based on the sensor data.

14. The mechatronic system of claim 1, wherein the data source comprises a server.

15. The mechatronic system of claim 1, wherein the actuator is configured to dampen movement.

16. The mechatronic system of claim 1, wherein the actuator is configured to actively adjust an angle between a first limb member and a second limb member.

17. A mechatronic system comprising:
   a prosthetic joint comprising:
      at least one sensor configured to gather data regarding a motion parameter of the prosthetic joint;
      an actuator configured to control movement of the prosthetic joint;

a memory storing a first set of instructions for controlling the actuator based on the sensor data;

a communication interface configured to communicate with a data source external to the prosthetic joint; and a processor configured to execute the stored first set of instructions, execution of the first set of instructions causing the processor to determine a first actuator control command based on the sensor data that controls movement of the prosthetic joint according to a first activity; and a data source external to the prosthetic joint containing a second set of instructions for controlling the actuator based on the sensor data, wherein the communication interface is configured to communicate with the data source to receive the second set of instructions;

wherein the memory is further configured to store the second set of instructions; and wherein the processor is further configured to receive and execute the second set of instructions and replace the first set of instructions in the memory with the second set of instructions, execution of the second set of instructions causing the processor to determine a second actuator control command based on the sensor data that controls movement of the prosthetic joint according to a second activity, the first actuator control command being different than the second actuator control command, and the first activity being different than the second activity.

18. The mechatronic system of claim 17, wherein the prosthetic joint is a lower limb prosthetic joint.

19. The mechatronic system of claim 17, wherein the data source comprises a network computing device selected from the group consisting of a server computer, a personal computer, a mobile computer, a personal digital assistant and a mobile telephone.

20. The mechatronic system of claim 17, wherein the data source comprises another prosthetic device.

21. The mechatronic system of claim 17, wherein the data source comprises a first computing device that is configured to communicate with a second computing device over a network.

* * * * *